(12) United States Patent
Wilson et al.

(10) Patent No.: US 9,763,744 B2
(45) Date of Patent: Sep. 19, 2017

(54) BIOPSY DEVICE WITH INTEGRATED OPTICAL SPECTROSCOPY GUIDANCE

(71) Applicant: UNIVERSITY HEALTH NETWORK, Toronto (CA)

(72) Inventors: Brian C. Wilson, Toronto (CA);
Anthony Taywon Kim, Toronto (CA);
Pablo A. Valdes, Hanover, NH (US);
Keith D. Paulsen, Hanover, NH (US);
David W. Roberts, Lyme, NH (US)

(73) Assignees: TRUSTEES OF DARTMOUTH COLLEGE, Hanover, NH (US);
UNIVERISTY HEALTH NETWORK, Toronto (CA)

( * ) Notice: Subject to any disclaimer, the term of this patent is extended or adjusted under 35 U.S.C. 154(b) by 422 days.

(21) Appl. No.: 14/367,829

(22) PCT Filed: Dec. 21, 2012

(86) PCT No.: PCT/CA2012/001197
§ 371 (c)(1),
(2) Date: Jun. 20, 2014

(87) PCT Pub. No.: WO2013/091090
PCT Pub. Date: Jun. 27, 2013

(65) Prior Publication Data
US 2015/0148629 A1    May 28, 2015

Related U.S. Application Data

(60) Provisional application No. 61/579,200, filed on Dec. 22, 2011.

(51) Int. Cl.
*A61B 6/00* (2006.01)
*A61B 19/00* (2006.01)
(Continued)

(52) U.S. Cl.
CPC ........ *A61B 19/5244* (2013.01); *A61B 5/0071* (2013.01); *A61B 5/0075* (2013.01);
(Continued)

(58) Field of Classification Search
CPC ..... A61B 19/5244; A61B 34/20; A61B 10/04; A61B 5/14556; A61B 5/6848;
(Continued)

(56) References Cited

U.S. PATENT DOCUMENTS

| 6,175,759 | B1 | 1/2001 | Chan et al. | ................... 600/431 |
| 7,613,504 | B2 | 11/2009 | Rowe | ............................ 600/476 |

(Continued)

FOREIGN PATENT DOCUMENTS

| WO | WO 2005/087092 | 9/2005 |
| WO | WO 2010/085348 | 7/2010 |
| WO | WO 2011/088571 | 7/2011 |

OTHER PUBLICATIONS

Extended European Search Report Issued in European Application No. 12859924, mailed on Sep. 15, 2015.
(Continued)

*Primary Examiner* — Sanjay Cattungal
(74) *Attorney, Agent, or Firm* — Norton Rose Fulbright US LLP

(57) ABSTRACT

An optical spectroscopy probe for providing optical spectroscopy guidance of a mechanical biopsy procedure, and a tissue biopsy device including an optical spectroscopy probe. The optical spectroscopy probe is positionable in a lumen of a mechanical biopsy device. The probe may enable optical spectroscopy guidance in biopsy procedures, include brain biopsy procedures.

15 Claims, 15 Drawing Sheets

(51) Int. Cl.
| | |
|---|---|
| A61B 10/02 | (2006.01) |
| A61B 17/34 | (2006.01) |
| A61B 5/00 | (2006.01) |
| A61B 5/1459 | (2006.01) |
| A61B 5/145 | (2006.01) |
| A61B 5/1455 | (2006.01) |
| A61B 10/04 | (2006.01) |
| A61K 49/00 | (2006.01) |
| A61B 34/20 | (2016.01) |
| A61B 90/00 | (2016.01) |
| A61B 90/11 | (2016.01) |

(52) U.S. Cl.
CPC .......... *A61B 5/0084* (2013.01); *A61B 5/1459* (2013.01); *A61B 5/14546* (2013.01); *A61B 5/14556* (2013.01); *A61B 5/489* (2013.01); *A61B 5/6848* (2013.01); *A61B 10/0275* (2013.01); *A61B 10/04* (2013.01); *A61B 17/3403* (2013.01); *A61B 34/20* (2016.02); *A61K 49/0017* (2013.01); *A61B 90/11* (2016.02); *A61B 2010/0208* (2013.01); *A61B 2010/045* (2013.01); *A61B 2034/2055* (2016.02); *A61B 2090/3945* (2016.02); *F04C 2270/041* (2013.01)

(58) Field of Classification Search
CPC ... A61B 5/14546; A61B 5/0071; A61B 5/489; A61B 5/1459; A61B 5/0084; A61B 5/0075; A61B 10/0275; A61B 17/3403; A61B 90/11; A61B 2034/2055; A61B 2090/3945; A61B 2010/0208; A61B 2010/045; A61K 49/0017; F04C 2270/041
USPC .................................................. 600/473–480
See application file for complete search history.

(56) References Cited

U.S. PATENT DOCUMENTS

| | | | | |
|---|---|---|---|---|
| 8,115,934 | B2* | 2/2012 | Boppart | A61B 5/0066 356/479 |
| 2003/0078504 | A1 | 4/2003 | Rowe | 600/476 |
| 2003/0191398 | A1* | 10/2003 | Motz | A61B 5/0075 600/478 |
| 2003/0232445 | A1* | 12/2003 | Fulghum, Jr. | A61B 5/0071 436/63 |
| 2004/0073120 | A1* | 4/2004 | Motz | A61B 5/0075 600/478 |
| 2005/0203419 | A1* | 9/2005 | Ramanujam | A61B 5/0075 600/473 |
| 2007/0093700 | A1* | 4/2007 | Wang | A61B 5/0059 600/317 |
| 2009/0219526 | A1 | 9/2009 | Davisson et al. | 356/301 |
| 2009/0326384 | A1 | 12/2009 | Bigio | 600/476 |
| 2009/0326385 | A1* | 12/2009 | Hendriks | A61B 5/0066 600/478 |
| 2012/0128264 | A1 | 5/2012 | Yazdanfar et al. | 382/274 |

OTHER PUBLICATIONS

Search Report and Written Opinion in PCT/CA2012/001197 dated Mar. 5, 2013.
International Preliminary Report on Patentability in PCT/CA2012/001197 dated Jun. 24, 2014.
Kim, A. et al. "A fiberoptic reflectance probe with multiple source-collector separations to increase the dynamic range of derived tissue optical absorption and scattering coefficients." Optics Express. vol. 18, No. 6, pp. 5580-5594. 2010.
Smith, J. S. et al. "Genetic Alteration in Adult Diffuse Glioma: Occurrence, Significance, and Prognostic Implications." Frontiers in Bioscience, d213-231. 2000.
Winger, M. J. et al. "Supratentorial anaplastic gliomas in adults." J. Neurosurg. 71:487-493. 1989.
Nitta, T. et al. "Prognostic Implications of the Extent of Surgical Resection in Patients with Intracranial Malignant Gliomas." Cancer. vol. 75, No. 11, pp. 2727-2731.
Gupta, T. et al. "Poor-prognosis high-grade gliomas: evolving an evidence-based standard of care." The Lancet Oncology. vol. 3, pp. 557-564. 2002.
Steck, J. et al. "Stereotactic Biopsy of Brainstem Mass Lesions." Surg. Neurol. vol. 43, pp. 563-568. 1995.
Coffey, R. J. et al. "Survival after Stereotactic Biopsy of Malignant Gliomas." Neurosurgery. vol. 22, No. 3, pp. 465-473. 1988.
Kim, A. et al. "Quantitative and Depth-Resolved Fluorescence Techniques for Intraoperative Guidance of Brain Tumor Resection Surgery."
Kim, A. et al. "Quantification of in vivo fluorescence decoupled from the effects of tissue optical properties using fiber-optic spectroscopy measurements." Journal of Biomedical Optics. 15(6), 067006.
Valdes, P. A. et al. "Quantitative fluorescence in intracranial tumor: implications for ALA-induced PpIX as an intraoperative biomarker." J. Neurosurg. 115(1): 11-17. 2011.
DeAngelis, L. M. et al. "Primary and metastatic brain tumors." Cancer Management: A Multidisciplinary Approach. Chapter 26. pp. 615-638.
IPRP issued in International Application No. PCT/CA2011/000090, dated Apr. 11, 2011.
IPRP issued in International Application No. PCT/CA2012/001197, dated Jul. 3, 2014.
International Search Report issued in International Application No. PCT/CA2011/000090.
International Search Report & Written Opinion issued in International Application No. PCT/CA2012/001197, dated Mar. 5, 2013.
Office Action issued in U.S. Appl. No. 13/575,236, dated Sep. 2, 2014.
Written Opinion Issued in PCT/CA2011/000090, dated Apr. 11, 2011.
Zysk, A. M. et al. "Clinical Feasibility of Microscopically-Guided Breast Needle Biopsy Using a Fiber-Optic Probe with Computer-Aided Detection." Technology in Cancer Research & Treatment. vol. 8, No. 5, pp. 315-321. 2009.
Response to Office Action for European Application No. 12859924.8, filed Apr. 12, 2016.

* cited by examiner

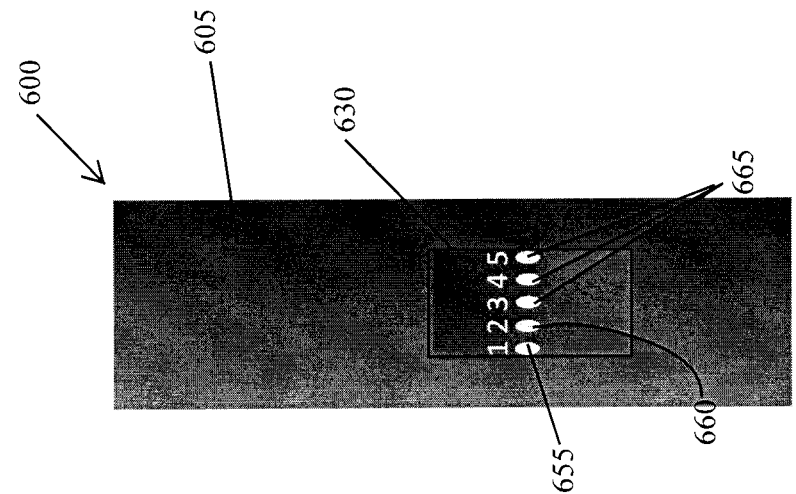
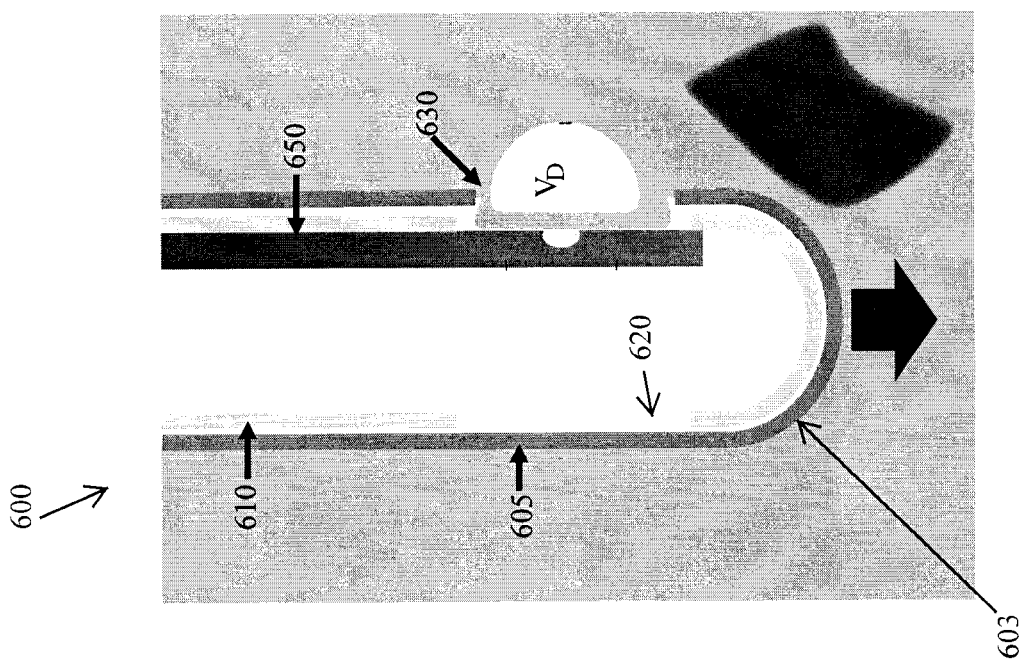
FIG. 5B
FIG. 5A

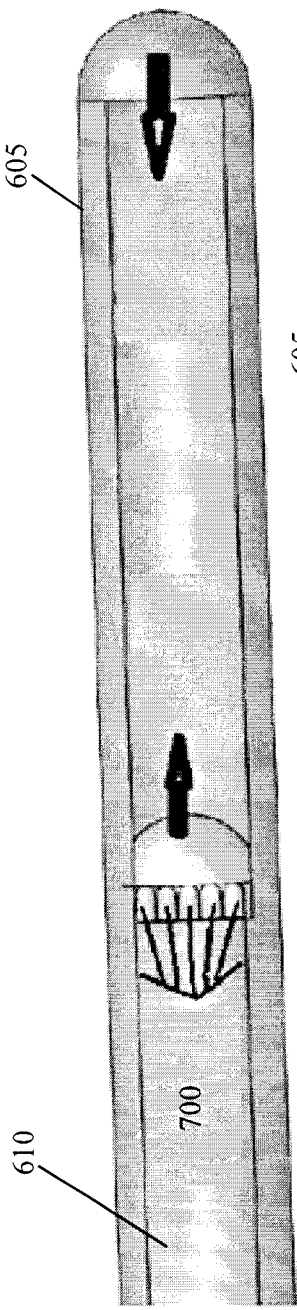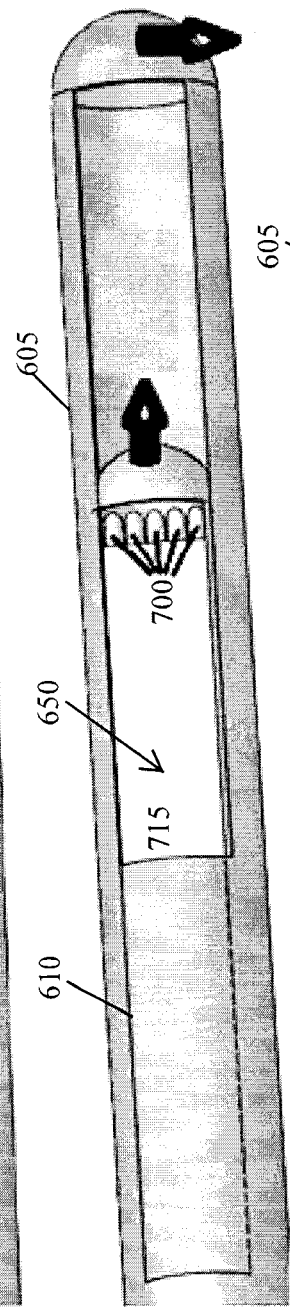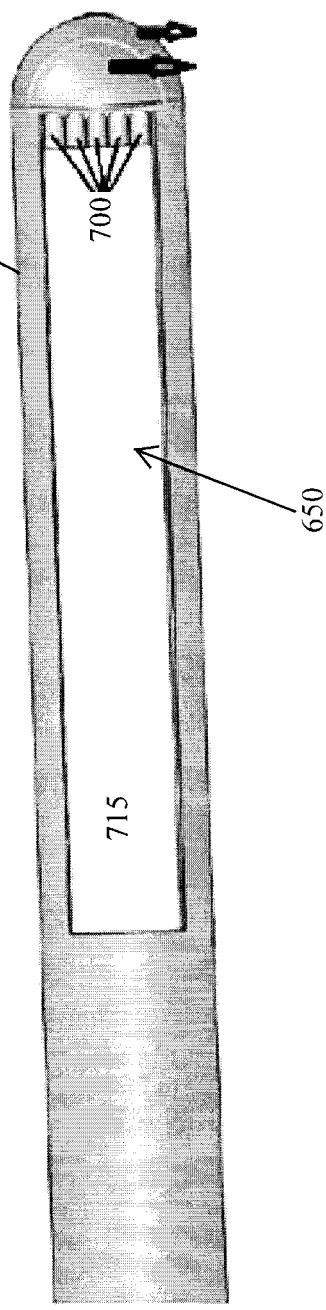

BIOPSY DEVICE WITH INTEGRATED OPTICAL SPECTROSCOPY GUIDANCE

CROSS-REFERENCE TO RELATED APPLICATION

This application is a national phase application under 35 U.S.C. §371 of International Application No. PCT/CA2012/001197 filed Dec. 21, 2012, which claims priority from U.S. provisional patent application No. 61/579,200, filed Dec. 22, 2011, the entirety of which are hereby incorporated by reference.

TECHNICAL FIELD

The present disclosure relates generally to devices, systems and methods for optical spectroscopy-guided biopsy, including devices, systems and methods that integrate an optical spectroscopy probe into a tissue biopsy device, for optical spectroscopy guidance of biopsy procedures.

BACKGROUND

Tissue biopsy is typically intended to find the most malignant tissue when cancer is suspected, so as to have an accurate diagnosis of the overall tumor, determine the patient's prognosis and/or obtain information to guide treatment decisions. Typically, a biopsy needle is introduced through the skin (or in the case of brain biopsy, a small hole is drilled into the skull) and is inserted to the depth of the suspected disease site. A tissue sample is drawn into the needle through a window at the needle tip using mechanical or pneumatic action.

Obtaining the sample of tissue accurately often requires image guidance and/or a stereotactic technique to localize the biopsy needle's sampling window to the desired biopsy location within the patient. Image guidance may be provided by a computed tomography (CT) or magnetic resonance imaging (MRI) scan. Even with such image guidance, the biopsy that is acquired may not be fully representative of a patient's disease state. Performing a biopsy of a glioma is an example illustrating this difficulty. A typical goal of glioma biopsy is to identify the most malignant (that is, the highest grade) sample; however, this is often complicated by the fact that gliomas by nature are spatially heterogeneous. Even with the aid of an MRI or CT scan to identify the gross location of the brain tumor, it is often difficult to acquire a biopsy representing the most malignant part of the tumor without further guidance. Further, such external imaging techniques may not provide sufficient spatial resolution to accurately determine whether the biopsy device is appropriate positioned at a desired biopsy target. For example, the spatial resolution of MRI may be on the order of a few mm, which may be insufficiently fine.

In situations such as a glioma biopsy, or other situations, more than one biopsy attempt may be required to acquire an elusive piece of tissue. This takes time and may be increasingly risky as more biopsies are taken, particularly for sensitive sites such as the brain. As well, since there is often a limit to the number of biopsies that a surgeon may acquire safely, there is typically more risk of missing critical tumor zones (i.e., under-estimation of malignancy) compared with open surgical acquisition of tissue.

There is also the issue of safety during these biopsy procedures. For example, if a large blood vessel is situated within the tissue sampling volume, there is risk of the surgeon tearing a part of the vessel during biopsy excision and so causing local hemorrhage.

SUMMARY

In some example aspects, the present disclosure provides an optical spectroscopy probe for providing optical spectroscopy guidance of a mechanical biopsy procedure, the optical spectroscopy probe being positionable in a lumen of a mechanical biopsy device, the optical spectroscopy probe may include: at least one optical detector at a probing region of the optical spectroscopy probe for receiving at least one of fluorescence emission wavelengths and reflectance wavelengths through a biopsy window of the biopsy device, the receiving being at least partially along an angled axis that is at a non-zero angle to a longitudinal axis of the optical spectroscopy probe; at least one fluorescence excitation source at the probing region for emitting fluorescence excitation light through the biopsy window, at least partially along the angled axis; and at least two broadband light sources at the probing region for emitting broadband wavelengths of light through the biopsy window, at least partially along the angled axis; wherein each of the at least one fluorescence excitation source and each of the at least two broadband light sources are at a respective known distance from each of the at least one optical detector.

In some examples, each of the at least one optical detector, the at least one fluorescence excitation source and the at least two broadband light sources may include an optical fiber, each optical fiber being configured to redirect emitted light from along the longitudinal axis to at least partially along the angled axis or to redirect received light from along the angled axis to at least partially along the longitudinal axis.

In some examples, each optical fiber may include an optical element for redirecting emitted light or received light.

In some examples, the optical element may include at least one of: a reflective surface, and a prism.

In some examples, the probe may include a substrate for supporting the at least one fluorescence excitation source and the at least two broadband light sources at the respective known distances from each of the at least one detector.

In some examples, at least one of the broadband sources may be at a distance from the at least one detector that is substantially equal to a distance between the at least one fluorescence excitation source and the at least one detector.

In some examples, there may be one detector, one fluorescence excitation source at a distance of about 260 μm from the detector, and two broadband sources each at a respective distance of about 260 μm and 520 μm from the detector.

In some examples, the fluorescence excitation source may be configured to emit fluorescence excitation light in the range of about 350 nm to about 750 nm.

In some examples, the fluorescence excitation source may be configured to emit fluorescence excitation light in the range of about 500 nm to about 750 nm.

In some examples, the fluorescence excitation source may be configured to emit fluorescence excitation light in the range of about 380 nm to about 420 nm.

In some examples, the detector may be configured to receive emission and/or reflectance wavelengths in the range of about 400 nm to about 850 nm.

In some examples, there may be a plurality of fluorescence excitation sources, each of the plurality of fluorescence excitation sources emitting a different range of fluorescence excitation wavelengths.

In some examples, the probe may be configured to be positionable in a lumen of a brain biopsy device.

In some examples, the probe may be configured to be positionable in a lumen of a breast biopsy device, a prostate biopsy device, a lung biopsy device, or a head and neck biopsy device.

In some example aspects, the present disclosure provides a tissue biopsy device that may include: a cannula body having defined a biopsy window for obtaining a mechanical biopsy of a probe target; and an optical spectroscopy probe positionable in a lumen of the cannula body, the optical spectroscopy probe including a probing region configured to emit and receive optical signals through the biopsy window for obtaining an optical spectrum of the probe target.

In some examples, the optical spectroscopy probe may include, at the probing region: at least one optical detector for receiving fluorescence emission or reflectance wavelengths from the probe target; at least one fluorescence excitation source for emitting fluorescence excitation light to the probe target; and at least two broadband light sources for emitting broadband wavelengths of light to the probe target; wherein each of the at least one fluorescence excitation source and each of the at least two broadband light sources are at a known distance from each of the at least one optical detector.

In some examples, the cannula body may include: an outer cannula defining the biopsy window; and an inner cannula positionable in a lumen of the outer cannula; the inner cannula having defined a cutting window with one or more cutting edges, the inner cannula being positionable to align the cutting window with the biopsy window; wherein the optical spectroscopy probe is positionable in a lumen of the inner cannula.

In some examples, the optical spectroscopy probe may be positionable away from the biopsy window to enable acquisition of a tissue sample through the biopsy window.

In some examples, the optical spectroscopy probe may be rotatable within the lumen of the cannula body.

In some examples, the optical spectroscopy probe may be removably positionable in the lumen of the cannula body.

In some examples, the biopsy window may be defined in a side wall of the cannula body and the optical spectroscopy probe may be configured to emit optical signals and receive optical signals at an angled direction that is at a non-zero angle to a longitudinal axis of the cannula body, through the biopsy window.

In some examples, the optical spectroscopy probe may be configured to communicate detected optical signals to a processor.

In some examples, the optical spectroscopy probe may be any one of the optical spectroscopy probes described above.

In some examples, the biopsy device may be a brain biopsy device.

In some examples, the biopsy device may be a breast biopsy device, a prostate biopsy device, a lung biopsy device, or a head and neck biopsy device.

In some example aspects, the present disclosure provides a method for characterizing a tissue intended for biopsy, the method may include: positioning an optical spectroscopy probe in a lumen of a mechanical biopsy device, a biopsy window of the mechanical biopsy device being positioned in a vicinity of the tissue; controlling the optical spectroscopy probe to emit and receive optical signals through the biopsy window for obtaining at least one of a fluorescence emission spectrum and a reflectance spectrum of at least one of: the tissue and a fluorophore coupled to and/or concentrated within the tissue; and using the obtained optical spectrum, calculating an optical property of the at least one of the tissue and the fluorophore, in order to characterize the tissue.

In some examples, the emitted optical signals may be emitted by at least one fluorescence excitation source and at least two broadband light sources, and the received optical signals may be received by at least one detector, and each of the at least one fluorescence excitation source and the at least two broadband light sources may be at a respective known distance from the at least one detector.

In some examples, the fluorophore may be a tumor tissue marker.

In some examples, the fluorophore may be aminolevulinic acid (ALA)-induced protoporphyrin IX (PpIX) or an ALA derivative-induced PpIX.

In some examples, the tissue may be characterized as a biopsy target or a tissue to avoid.

In some examples, the biopsy target may be a tumor tissue and the tissue to avoid may be a large blood vessel.

In some examples, characterizing the tissue may include: using the reflectance spectrum, determining a hemoglobin concentration of the tissue, based on a known optical absorption spectrum of hemoglobin; and determining if the hemoglobin concentration indicates the presence of a large blood vessel.

In some examples, characterizing the tissue may include determining a tumor grade of the tissue, based on the fluorescence emission spectrum.

In some examples, characterizing the tissue may include determining whether the tissue is a tissue with highest tumor grade.

In some examples, the method may include, if the tissue is characterized as a tissue to avoid: providing a notification to avoid biopsying the tissue.

In some examples, the method may include, if the tissue is characterized as a biopsy target: obtaining a biopsy sample through the biopsy window.

In some examples, the method may include: prior to obtaining the biopsy sample, positioning the optical spectroscopy probe away from the biopsy window.

In some examples, the biopsy device may be a brain biopsy device.

In some examples, the biopsy device may be at least one of: a breast biopsy device, a prostate biopsy device, a lung biopsy device, and a head and neck biopsy device.

In some examples, the tissue may be characterized as a tumor tissue or a non-tumor tissue.

In some example aspects, the present disclosure provides a system for providing optical spectroscopy guidance of a mechanical biopsy procedure, the system may include: any one of the optical spectroscopy probes or biopsy devices described above; a processor coupled to the optical spectroscopy probe, the processor communicating control signals to the optical spectroscopy probe for controlling emission of light from the optical spectroscopy probe and the processor receiving optical signals from the optical spectroscopy probe indicative of at least one of a fluorescence emission spectrum and a reflectance spectrum of a probe target, the processor being configured to calculate an optical property of the probe target using the optical spectrum; and an output device coupled to the processor for providing an output based on the calculated optical property.

In some examples, the processor may be further configured to characterize the probe target as a biopsy target or a tissue to avoid, based on the calculated optical property.

In some examples, the biopsy target may be a tumor tissue and the tissue to avoid may be a blood vessel.

In some examples, the processor may be further configured to characterize the probe target by: using the reflectance spectrum, determining a hemoglobin concentration of the tissue, based on a known optical absorption spectrum of hemoglobin; and determining if the hemoglobin concentration indicates the presence of a large blood vessel.

In some examples, the processor may be further configured to characterize the probe target by determining a tumor grade of the probe target, based on a determination of a fluorophore concentration or presence, using the fluorescence emission spectrum.

In some examples, the processor may be further configured to characterize the probe target by determining whether the probe target is a tissue with highest tumor grade.

In some examples, the processor may be further configured to, if the probe target is characterized as a tissue to avoid, cause the output device to output a notification to avoid biopsying the tissue.

In some examples, the processor may be further configured to characterize the probe target as a tumor tissue or a non-tumor tissue.

BRIEF DESCRIPTION OF THE DRAWINGS

Reference will now be made to the drawings, which show by way of example embodiments of the present disclosure, and in which:

FIGS. 5A-5C illustrate an example optical spectroscopy probe positioned in an example biopsy device;

FIGS. 8A-8C illustrate how the example optical spectroscopy probe of FIG. 6 may be positionable in an example biopsy device;

It will be noted that throughout the appended drawings, like features are identified by like reference numerals.

DETAILED DESCRIPTION

Figure 1A:
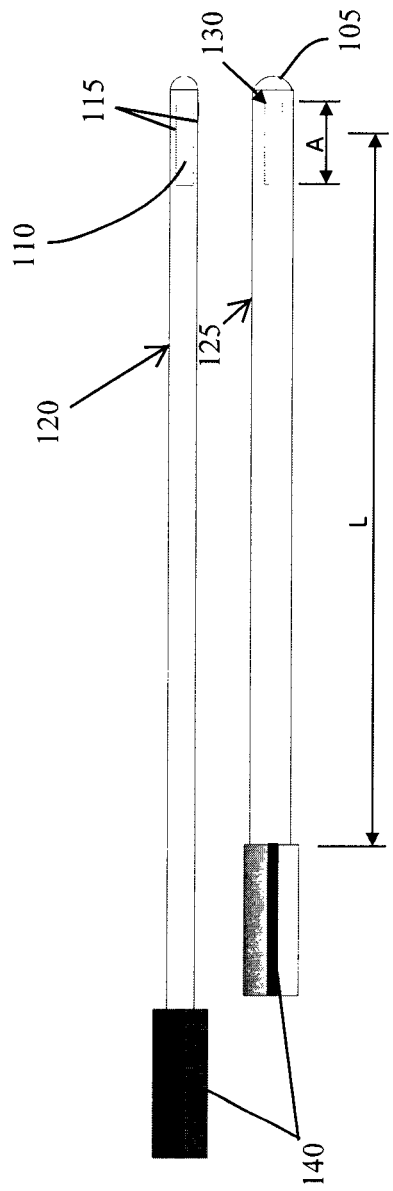
FIGS. 1A and 1B show and example biopsy needle that may be provided with optical guidance, in accordance with the present disclosure.

In various example aspects and embodiments, the present disclosure may provide a device capable of interrogating (i.e., obtaining information from) a suspect volume of tissue about to be biopsied while the biopsy needle is in place, but prior to the biopsy acquisition. The device may interrogate the tissue in situ in the vicinity of (e.g., immediately outside) the biopsy window, in order to obtain information that may help in determining if the potential biopsy sample is representative of the suspected disease. As well, this interrogation may provide information that may help in determining if a large blood vessel is in close proximity to the cutting window and at risk of being cut or damaged by the biopsy procedure. The present disclosure may provide devices and methods suitable for interrogating the potential biopsy tissue, for example using an optical spectroscopy probe permanently or removably integrated with the biopsy needle itself, which may help the surgeon in identifying desired biopsy sites within the patient more rapidly and with increased patient safety.

Optical spectroscopy techniques have been shown to be useful for the diagnosis and detection of disease, and thus may be useful for in situ evaluation of potential biopsy sites (prior to the actual tissue excision). For example, fluorescence may be used to detect cancer by marking tumor cells with an appropriate fluorescing agent. An example of this is the oral administration of 5-aminolevulinic acid (5-ALA) to promote the over-production of protoporphyrin IX (PpIX) (also referred to as ALA-induced PpIX or ALA-PpIX) in glioma cells. Other ALA derivatives may also be used to induce production of PpIX in tissues. PpIX typically fluoresces bright-red under violet-blue illumination, allowing for the identification of microscopic, otherwise occult glioma cells during surgical resection of tumors, such as gliomas [1]. Optical spectroscopy may also be used to quantify the presence of relatively strong optical absorbers in tissue, such as hemoglobin in blood [3]. Therefore, optical techniques may be employed to detect blood vessels within a detection volume.

Optical spectroscopic techniques may be further enabled by the use of fiber optic technology. For example, fiber optics may be routed from a control system that may transmit light through an optical fiber to the detection volume, and a receiver fiber optic may receive the spectroscopic response from tissue in the detection volume and transmit the response signal to a detector in the control system. Optical spectroscopy, which may be implemented using fiber optics, may thus be useful for providing in situ guidance to tissue biopsy acquisition.

In some examples, the present disclosure describes the use of fluorescence to detect cancer by marking tumor cells with an appropriate fluorescing agent, and detecting the diseased tissue using an optical probe (e.g., a fluorescence spectroscopy probe) that may be integrated into a biopsy device.

In some examples, the present disclosure also describes the use of optical spectroscopy to detect blood vessels in a target volume of biopsy tissue. For example, if there is extensive vasculature in the vicinity of the biopsy window, the optical information may be used to generate information warning the operator against taking a tissue biopsy sample at that location, since there may be a risk of hemorrhage. Thus, integration of optical spectroscopy guidance in a biopsy device may provide a real-time guidance tool that may enable on-the-spot determination on the presence and/or degree of malignancy, which may help to enable a faster and/or safer procedure. This may be used in any suitable intraoperative biopsy procedure, but will be described in detail here using the example of brain tumors. It should be understood that the present disclosure is not limited to use in brain tumors.

Figure 1B:
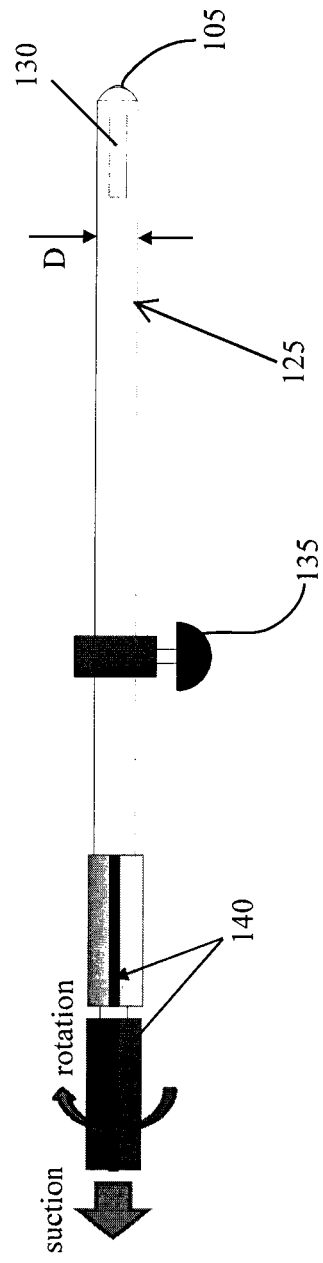

Stereotactic biopsies of the brain are typically acquired when surgical resection is not indicated or is considered to be too risky but a definitive diagnosis is still desired. A diagram of an example stereotactic biopsy needle 100 is shown in FIGS. 1A and 1B. FIG. 1A shows the example needle 100 with an inner cannula 120 separated from an outer cannula 125, while FIG. 1B shows the needle 100 with the cannulas 120, 125 assembled. Such a needle 100 may be suitable for biopsy of brain tissue, for example. In this example the needle 100 includes a tip 105 located at a distal end of the needle 100. The tip 105 may be rounded, to reduce the risk of severing delicate brain blood vessels as the tip 105 pushes through brain tissue. A lateral cutting window 110 may be provided at or near the 105, the window 110 being surrounded by one or more cutting edges 115 on the inner cannula 120 that may rotate relative to the outer cannula 125 (with a matching window 130) that may be in direct contact with the tissue.

In operation, suction (typically about 1 cc of air) may be applied through the needle bore defined in the inner cannula 120, in order to draw tissue through the windows 110, 130. The tissue that is now within the needle bore may be cut by rotation of the inner cannula 120 such that the cutting edge(s) 115 may sever the tissue drawn within the needle bore. Such a procedure may be referred to as a mechanical biopsy procedure, and the biopsy needle 100 may be referred to as a mechanical biopsy needle or a mechanical biopsy device.

The needle 100 may include other features such as a needle stop 135 (which may or may not be adjustable), which may be used to limit the depth of penetration of the needle 100. The needle 100 may also include an indicator 140 located at or near a proximal end of the needle 100. The indicator 140 may include indication arrows provided on hubs of the inner and outer cannulas 120, 125, that, when the arrows are aligned, may indicate that the windows 110, 130 are aligned and open to draw in tissue.

In this example, the needle 100 may have any suitable length L and the windows 110, 130 may have similar or different lengths, typically similar lengths A. The lengths L and A may be selected to suit the application. The needle 100 may have a cross-sectional diameter selected to suit the application, for example a cross-sectional diameter D of about 2.11 mm.

Stereotactic biopsies of the brain typically include placing a biopsy needle 100 carefully into the brain (typically via a small hole through the skull) to a point in the cranium that is determined by pre- or intra-operative radiological images.

Figure 1C:
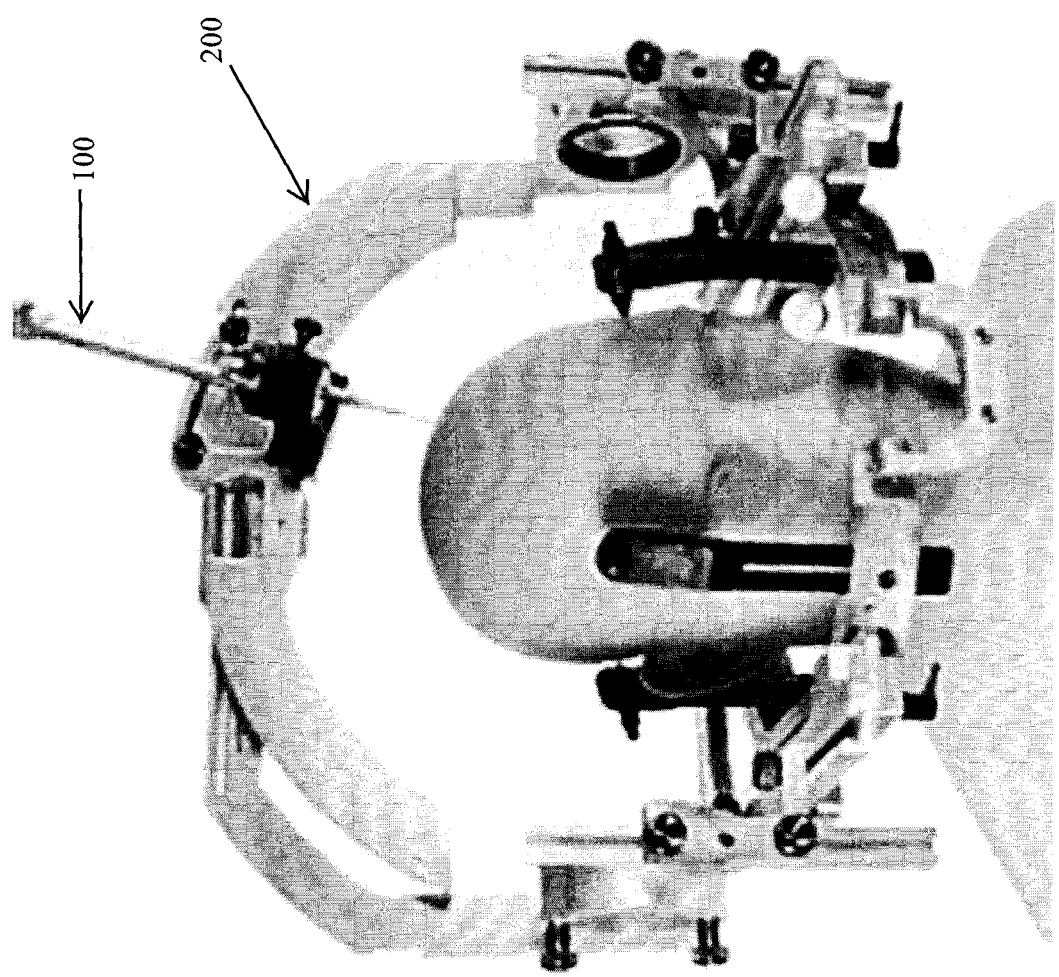
FIG. 1C shows an example frame for assisting in a brain biopsy procedure.

FIG. 1C shows an example stereotactic frame 200 (from Ad-Tech Medical Instrument Corporation) that may be mounted to the patient's head that may be used to more accurately guide the needle 100, for example as determined by pre-operative imaging. In some examples, a frameless image-guidance system (not shown) may be used instead of the frame 200.

Typically, once the needle 100 is placed (and the location may be confirmed using suitable imaging methods), mild suction may be applied to bring tissue into the cutting window 110, the biopsy may be cut, and the tissue may be taken to be histologically analyzed. If intraoperative analysis is desired, a frozen-section of cytological smear analysis typically may take additional time, for example about 10 to 25 minutes, increasing the time of the overall biopsy procedure. Reducing these times may be a desirable, yet challenging clinical problem.

Figure 2A:
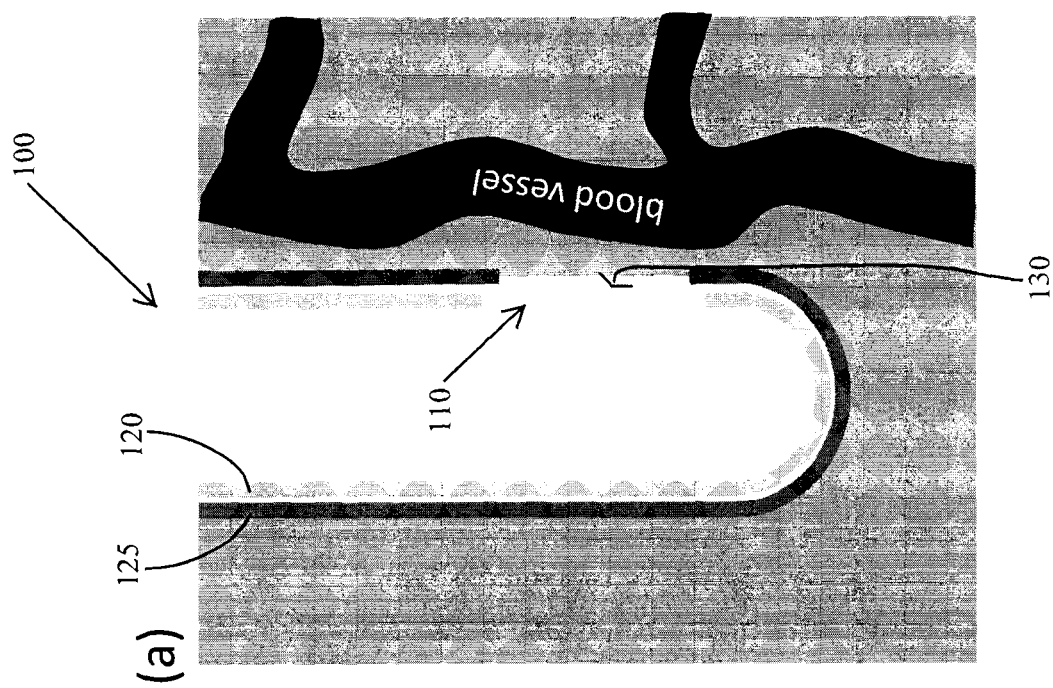
FIGS. 2A and 2B illustrate a biopsy procedure with risk of causing a hemorrhage.
Figure 2B:
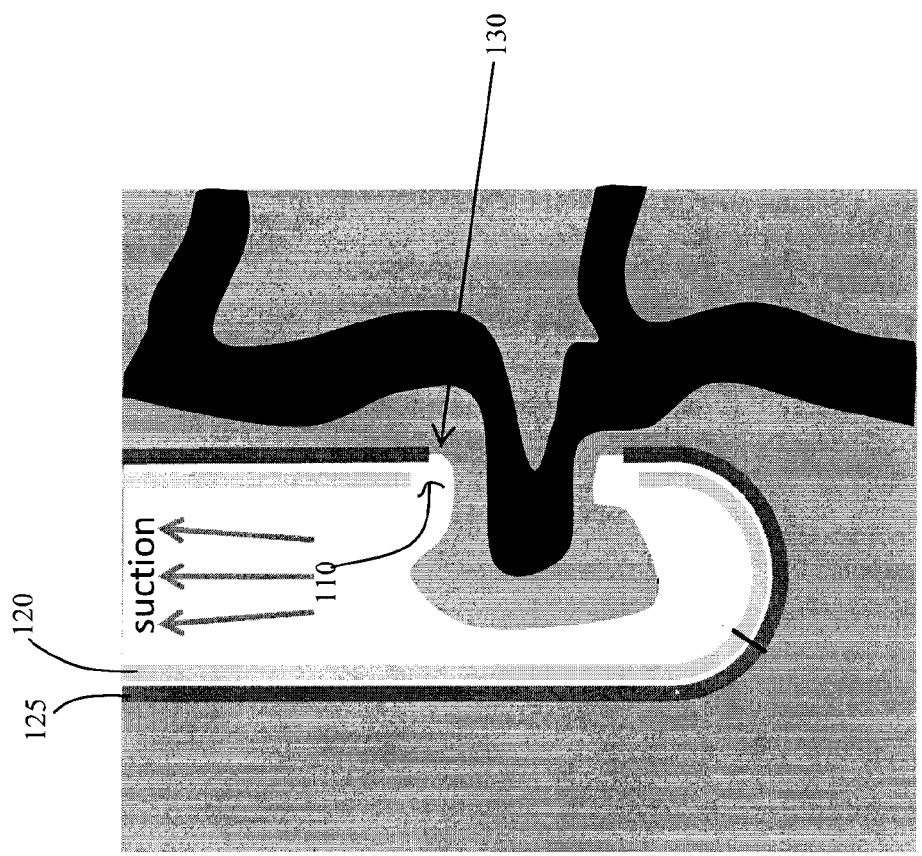

During biopsy procedures, particularly in delicate tissue such as brain tissue, there may be a risk of unintentional damage to other tissues. For example, as shown in FIGS. 2A and 2B, if a blood vessel (particularly a relatively large blood vessel) is situated within or near the tissue sampling volume (e.g., situated near the location of the open cutting window 110), there is risk that the blood vessel may be drawn into the cutting window 110 (FIG. 2B) without the surgeon's knowledge and subsequently unintentionally severed by the cutting edge(s) 115, which may lead to a brain hemorrhage.

The disclosed methods and systems may enable the use of quantitative optical spectroscopy in conjunction with biopsy procedures.

In some examples, the present disclosure describes the use of fluorescence to detect cancer by marking tumor cells with an appropriate fluorescing agent, and detecting the diseased tissue using a fluorescence spectroscopy probe that may be integrated into a biopsy excision needle.

In some examples, the present disclosure describes the use of optical spectroscopy to detect blood vessels in a target volume of biopsy tissue. For example, if there is extensive nearby vasculature, optical information may be used to warn against biopsying when there is a risk of hemorrhage.

In some examples, the present disclosure may provide quantitative optical spectroscopy that may be used as a substantially real-time, intraoperative guidance tool to provide an on-the-spot determination on the presence and/or grade of tumor malignancy, which may help to enable a faster, more effective and/or safer procedure. This may be used in any intraoperative procedure. The present disclosure describes use in the specific example of brain tumors. It should be understood that the present disclosure is not limited to use for biopsy of brain tissue (e.g., for diagnosis of brain tumors).

In some examples, the present disclosure may enable substantially real-time and in situ evaluation of tissue malignancy prior to biopsy excision. This may be useful, for one or more reasons, which may include one or more of the following: faster procedures may be generally more desirable; reducing the number of biopsies may be generally desirable; and obtaining tissue from the region of tumor with the highest (or as high as might be reasonably detected) grade or degree of malignancy may be generally desirable, for example in order to determine the appropriate treatment.

By using a fluorescent marker of tumor malignancy, such as, for example, 5-aminolevulinic acid-induced protoporphyrin IX (PpIX) (or any other suitable marker), that preferentially accumulates in brain tumors [1], together with a quantitative fluorescence (qF) fiberoptic-based probe, as presently disclosed, for determining absolute PpIX concentration at the intended biopsy site, the surgeon may be provided with a substantially real-time evaluation of tissue malignancy. This may help the surgeon to more judiciously and/or rapidly select optimal sites to biopsy, which in turn may help to reduce the risk to the patient.

Figure 3:
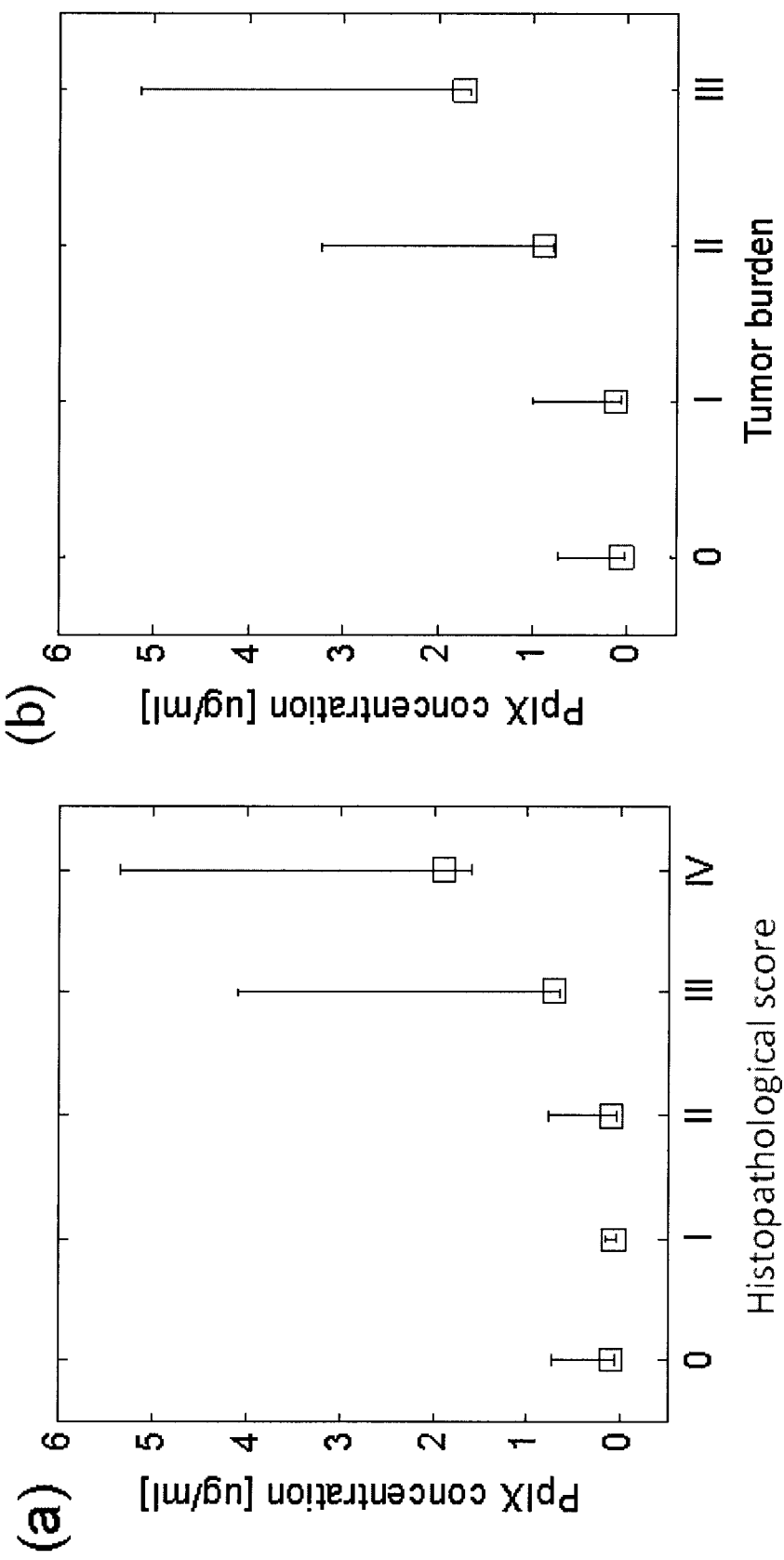
FIGS. 3a and 3b are charts illustrating the correlation of PpIX with histopathological score and tumor burden.

As shown in FIGS. 3A and 3B, PpIX concentration has been found to be correlated to both histopathological score and tumor burden in a sample population of glioma biopsies. FIG. 3A is a chart showing PpIX concentration, [PpIX], plotted against histopathological score. FIG. 3B is a chart showing [PpIX] versus tumor burden. Square symbols are the median value and the error bars represent the interquartile range. Both curves show a positive correlation to PpIX concentration.

Other suitable markers may be used. In some examples, such as where the tissue itself exhibits fluorescence properties, markers may not be necessary.

Tissue fluorescence quantification may be achieved using various fiberoptic devices; however, this typically is dependent on an accurate biophysical model of the detection geometry. A challenge in using fluorescence for medical diagnostics and therapeutics may be in making the measurements accurately quantitative. Measured fluorescence signals are typically affected by variations in the tissue absorption and transport scattering properties (i.e., tissue optical properties), whereas often the objective may be to quantify the fluorescence based on fluorophore concentration alone.

Figure 4:
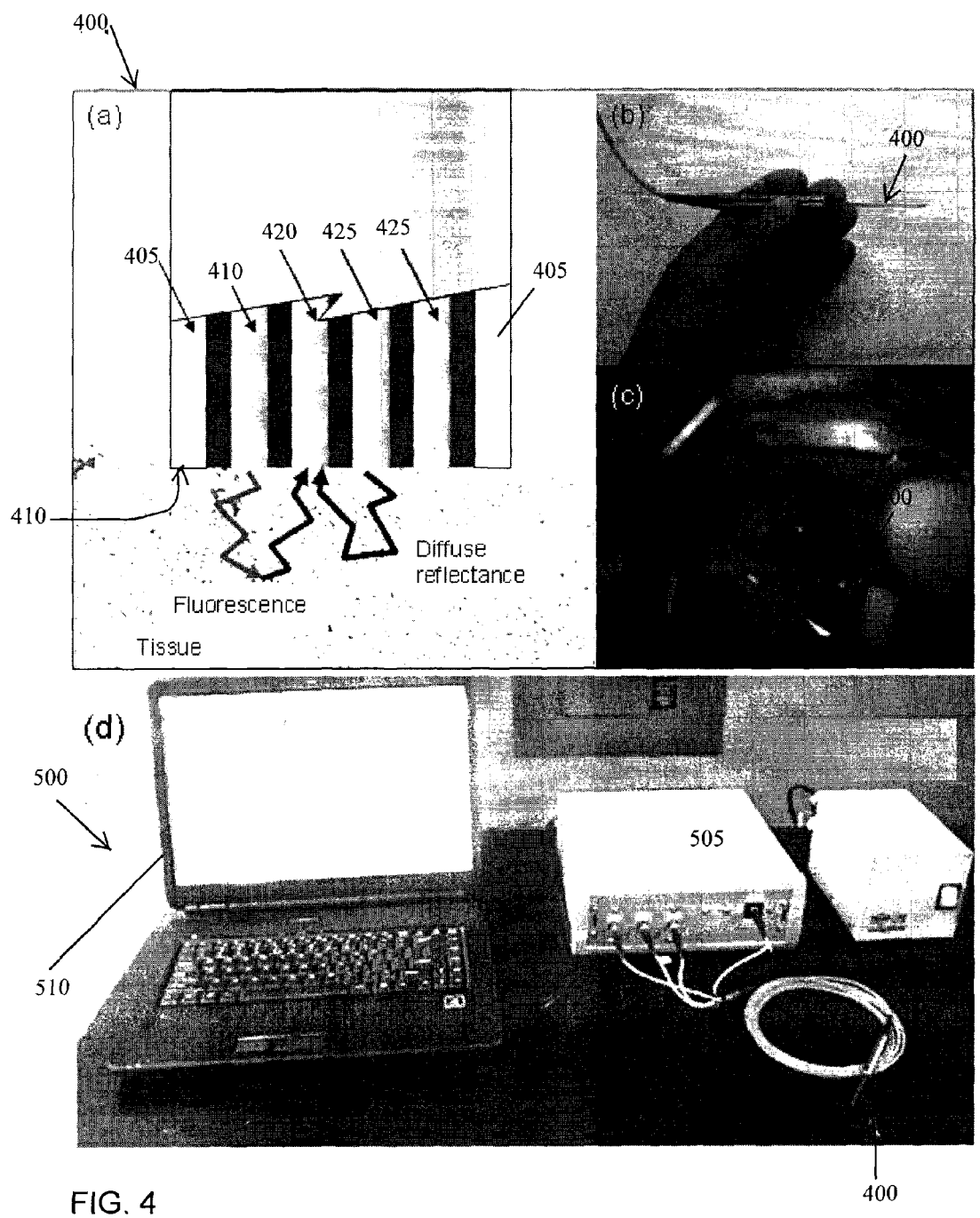
FIGS. 4a-4d illustrate an example optical spectroscopy probe and system.

FIG. 4 shows diagrams and images of an example device and system suitable for in vivo quantification of fluorescence in tissue. In some examples, this device and system may be similar to that described in PCT Publication No. 2011/088571, the entirety of which is hereby incorporated by reference. The device may include an optical spectroscopy probe, which may operate in the manner described in PCT Publication No. 2011/088571, for example.

An example description of the optical spectroscopy probe and its operation is now provided, to assist in understanding the present disclosure. In the example shown in FIG. 4A, the optical spectroscopy probe may be designed to contact a probe target (e.g., a target tissue or target fluorophore), in order to perform spectroscopic measurements. Although an end-on configuration, which may be suitable for open surgical procedures, is shown here, a different configuration that may be more suitable for biopsy procedures may be used, as described further below. FIG. 4A illustrates a cross-section of a distal tip of an example fiberoptic-mediated optical spectroscopy probe 400. Such a probe 400 may be suitable for measuring tissue fluorescence and/or diffuse reflectance spectra by sequentially exciting the probe target with fluorescence excitation light and broadband white light.

The probe 400 may include a probe body 405, such as a sheath. The body 405 may have a distal tip 410 in which optical fibers may be positioned for emitting and receiving optical signals. Although FIG. 4A shows an example where the tip 410 is configured for direct contact with a probe target, other configurations may be suitable, as described further below.

The probe 400 may include at least one fluorescence excitation source 415, such as a fluorescence excitation optical fiber. The fluorescence excitation source 415 may emit fluorescence light for exciting the probe target (e.g., a fluorescence marker coupled a target tissue and/or the tissue itself where the tissue has fluorescence properties). The probe 400 may also include at least one detector 420, such as a detector optical fiber, for detecting fluorescence emission and/or reflectance wavelengths from the probe target. For example, fluorescence signals emitting and/or reflected by the fluorescence marker and/or tissue may be detected by the detector 420. The probe may also include at two broadband light sources 425, such as two white light fibers (which may be similar to or different from each other) for providing broadband wavelengths of light to the probe target. The sources 415, 425 and the detector(s) 420 may be at fixed, known distances from each other, which may enable calculations to obtain quantitative measurements of the probe target.

In the example of FIG. 4A, the sources 415, 425 and the detector(s) 420 may be configured in a substantially linear arrangement, with a single fluorescence excitation source 415, a single detector 425 and two broadband light sources 425. The body 405 in this example may be a stainless steel sheath with a diameter of about 1.1 mm. The sources 415, 425 and the detector(s) 420 may be provided as optical fibers that may be potted within the body 405, for example using a suitable material such as a black epoxy.

This example qF probe 400 may sequentially emit fluorescence-excitation light and white light through the sources 415, 425 and to the probe target to enable acquisition of the fluorescence and diffuse reflectance spectra, respectively. FIG. 4B is a photograph of an example handheld probe 400. FIG. 4C is an image showing example use of the probe 400 for acquiring a measurement during glioma resection surgery.

FIG. 4D shows an example system 500 that may be suitable for operating the probe 400 and for obtaining measurements from the probe 400. The system may be similar to that described in PCT Publication No. 2011/088571. The system may include a control system 505 for transmitting signals to and receiving signals from the probe 400. The control system 505 may be used to control optical signals to the probe 400, and may also contain a spectrometer that detects optical signals from the probe 400.

The control system 505 may communicate with a processor 510 (e.g., a laptop computing device). The processor 510 may, based on a diffusion theory model of light transport in tissue, calculate quantifiable values to make a quantitative measurement of the tissue concentration of a fluorescent marker (e.g., PpIX) based on fluorescence and reflectance spectral measurements from the control system 505. In addition to fluorescence quantification, other parameters may be calculated by the processor 510 using the reflectance measurements, including tissue oxygenation ($StO_2$), hemoglobin concentration ($[Hb]$) and a metric of the optical scatterers in tissue such as cells and collagen (e.g., as described in [4]), among others.

Figure 5C:
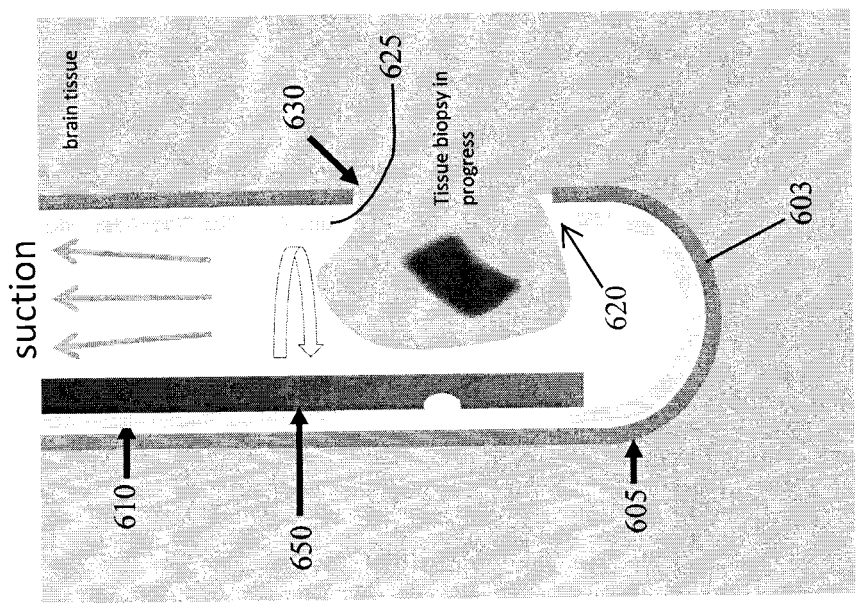

FIGS. 5A-5C are schematics showing close-up views of a distal tip 603 of an example biopsy device 600 including an optical spectroscopy probe 650. The biopsy device 600 may be a mechanical biopsy device 600 for mechanically obtaining a biopsy sample.

The biopsy device 600 may include an outer cannula 605 and an inner cannula 610, each having a respective lumen. The inner cannula 610 may be rotatably positioned (e.g., inserted) in the lumen of the outer cannula 615. Similar to the biopsy needle 100 described above, the inner cannula 610 may define a cutting window 620 with one or more cutting edges 625. The inner cannula 610 may be rotatable with respect to the outer cannula 605, in order to align the cutting window 620 with a biopsy window 630 defined in the outer cannula 605.

The optical spectroscopy probe 650 may be positionable in the lumen of the device 600 (e.g., the lumen of the inner cannula 610). The optical spectroscopy probe 650 may be permanently or removably positioned in the lumen. For example, the optical spectroscopy probe 650 may be attached to or otherwise fixed to the inner wall of the inner cannula 610, such that the optical spectroscopy probe 650 may be moved within the outer cannula 605 by rotation and/or sliding of the inner cannula 610, for example. The optical spectroscopy probe 650 may be positionable (e.g., by rotation and/or sliding of the inner cannula 610 or of the optical spectroscopy probe 650 itself) such that optical components positioned at a probing region 653 (e.g., at a distal end of the optical spectroscopy probe 650), as described below, may emit and receive optical signals through the biopsy window 630. For example, FIG. 5B shows the optical spectroscopy probe 650 positioned such that its optical components are viewable through the biopsy window 630.

Similar to the probe 400 described above, the probe 650 may, at its probing region 653, include at least one fluorescence excitation source 655 (e.g., a fluorescence excitation optode, formed by an optical fiber) for emitting fluorescence light to excite a probe target (e.g., a fluorescence marker coupled to and/or concentrated within a target tissue and/or the target tissue itself where the tissue has fluorescence properties), at least one detector 660 (e.g., a detector optode, formed by an optical fiber) for detecting fluorescence emission and/or reflectance wavelengths from the probe target; and at least two (in this example, three are shown) broadband light sources 665 (e.g., white light optodes, formed by optical fibers) for providing broadband wavelengths of light to the probe target. Each of the sources 655, 665 and the detector(s) 660 may be in communication with a control system 505 and a processor 510, for controlling emission of light from the sources 655, 665 and for receiving detected optical signals from the detector(s) 660.

The sources 655, 665 and the detector(s) 660 may be at fixed, known distances from each other (e.g., having a distance of about 50 μm or less to about 500 μm or more between neighboring sources 655, 665 and detector(s) 660, for example about 100 μm to about 300 μm, for example about 260 μm), which may enable calculations (such as described in PCT Publication No. 2011/088571) to obtain quantitative measurements of the probe target. These known distances may be selected to match the expected fluorescence spectra to be detected. For example, for detecting fluorescence of ALA-PpIX, the fluorescence excitation source 655 may be at a distance of about 260 μm from the detector 660, one broadband light source 665 may be at a distance of about 260 μm from the detector 660, and a second broadband light source 665 may be at a distance of about 520 μm from the detector 660. Other distances may be selected to better match detection of other fluorescence spectra (e.g., other fluorophores and/or other fluorescing tissues).

In an example optical spectroscopy probe 650, excitation light may be emitted from the sources 655, 665 at the probing region 653 and resulting reflectance and/or emission optical signals from the probe target (e.g., target tissue or fluorophore) may be received at the detector(s) 660. In this way, measurements of the fluorescence and/or reflectance (e.g., broadband reflectance) may be obtained. Applying an appropriate model of light interaction with tissue (such as described in PCT Publication No. 2011/088571 and elsewhere), the quantitative fluorescence, absorption and/or transport scattering properties of the probe target may be determined, as well as other physiological metrics such as tissue oxygenation and hemoglobin concentration.

In some examples, the optical spectroscopy probe 650 may communicate (e.g., via fiber optic connections) with a processor (e.g., in the control system 505 and/or the processor 510), which processor may communicate control signals for controlling the optical spectroscopy probe 650 (e.g., to control emission of fluorescence and broadband light and/or for data acquisition) and may receive optical signals from the optical spectroscopy probe 650, which optical signals may be indicative of the optical spectrum of the probe target (e.g., the target tissue and/or the fluorophore coupled to and/or concentrated within a tissue). The processor may then carry out appropriate calculations using the optical spectrum. The processor may implement appropriate algorithms to calculate one or more optical properties of the probe target (e.g., to derive the quantitative fluorescence of the probe target), which may be used to characterize the probe target. For example, the probe target may be characterized as a biopsy target (in which case output may be provided via one or more output devices, such as a display, that a biopsy sample may be acquired) or may be characterized as a tissue to avoid (in which case notification may be provided via the output device(s) that biopsy of the target should be avoided). The processor may communicate with the output device(s) and may provide a user interface (e.g., a graphical user interface) to control one or more settings of the data acquisition and/or to provide raw or processed data to the user.

In the example of FIG. 5B, the sources 655, 665 and the detector(s) 660 may be configured in a substantially linear arrangement. Other arrangements (e.g., circular, triangular or other non-linear arrangements) may be suitable, and may provide advantages such as space savings, for example. For example, the fibers may be arranged in a circular, staggered or random configuration, as long as their relative distances are fixed and defined. In some examples, it may be useful to have at least one broadband light source 665 at substantially the same distance from a detector 660 as at least one fluorescence excitation source 655.

As described in PCT Publication No. 2011/088571, for example, It may be useful to have at least two broadband light sources 665, each at a respective different distance from the detector 660, in order to obtain sufficient optical information from the probe target in order to solve the appropriate equations for obtaining quantitative fluorescence information. There may be more than one fluorescence excitation source 655 provided, with possibly different fluorescence excitation wavelengths for different fluorescence excitation sources 655. The use of different excitation wavelengths may allow for excitation of a variety of fluorescence markers (e.g., different fluorophores). In some examples, it may be useful to have all fluorescence excitation sources 655 substantially the same distance away from a detector 660.

In an example operation of the optical spectroscopy probe 650, the sources 655, 665 sequentially emit fluorescence excitation light and broadband light to the probe target and the detector 660 may receive the resulting fluorescence and diffuse (or broadband) reflectance spectra. The fluorescence spectrum may depend on parameters including the absorption and transport scattering coefficients of the probe target (e.g., the target tissue or fluorophore) at the excitation wavelength and the emission wavelength, and fluorophore content. The reflectance spectrum may depend on the wavelength-dependent absorption and scattering coefficients of the probe target. Based on a diffusion theory model, or other suitable or substantially equivalent models of light transport in tissue, these quantities may be calculated from the detected fluorescence and reflectance measurements. As well as fluorescence quantification being achieved, other useful parameters may be calculated from the data, such as tissue oxygenation, hemoglobin concentration and a metric of the abundance of optical scatterers in tissue such as cells, organelles and the extracellular matrix. Such information may be useful for identifying or characterizing the probe target. For example, such information may be useful for determining whether the probe target is a desired biopsy target.

The fluorescence excitation source(s) 655 may emit excitation optical signals having wavelengths in the range of about 350 nm or less to about 750 nm or more, for example about 500 nm to about 750 nm, or about 380 nm to about 420 nm, or about 405 nm. The excitation wavelength may be elected based on known characteristics of the target (e.g., target tissue or fluorophore) being interrogated. For example, the values provided about may be suitable to excite ALA-PpIX. Other wavelengths may be selected to match other fluorophores and/or other tissue characteristics.

The detector may be configured to receive emission and/or reflectance wavelengths in any suitable range (e.g., in the range of about 400 nm to about 850 nm), for example to suit the expected optical properties of the interrogated tissue. In some examples, the range of reflectance spectrum detected may correspond to the expected optical characteristics of the target tissue. For example, the reflectance spectrum may be detected to include at least the range of expected hemoglobin absorption (e.g., about 400 nm to about 700 nm). The reflectance spectrum may be used to correct the fluorescence measurement and/or to determine any distortion in reflectance that might be indicative of the presence of a large blood vessel in the detection volume, for example.

Since the biopsy window 630 may be positioned on the biopsy device 600 to be side-facing (that is, having a normal that is at least partially transverse to the longitudinal axis of the device 600, and which may also be referred to as non-axial-facing or transverse-facing) rather than end-on (that is, having a normal that is substantially aligned with the longitudinal axis of the device 600, and which may also be referred to as axial-facing or straight-facing), it may be useful for the probe 650 to be configured to obtain optical measurements through the side-facing biopsy window 630. For example, the optical spectroscopy probe 650 may be configured (e.g., by configuration at the probing region 653) in order to emit optical signals to and receive optical signals from a direction that passes through the biopsy window 630 (e.g., a direction at least partially transverse to the longitudinal axis of the device 600). For example, the optical spectroscopy probe 650 may be configured to emit and receive optical signals at a non-zero angle from the longitudinal axis, for example an approximately 90° angle.

In the example of FIG. 5A, the probe 650 may be configured to obtain optical measurements from the probe target in a detection volume $V_D$ in a region located laterally from the longitudinal axis of the biopsy device 600 (e.g., at a non-zero angle from the longitudinal axis, such as at approximately 90°). Typically, the detection volume $V_D$ at a given position and orientation of the biopsy device 600 may overlap with the region that would be biopsied if a tissue biopsy were to be carried out with the biopsy device 600 in that position and orientation. The device 600 may be advanced (as indicated by arrow at the distal tip 603) while the optical spectroscopy probe 650 is positioned at the biopsy window 630, in order to obtain measurements in substantially real-time as the device 600 is maneuvered in the patient. For example, as the device 600 is advanced, the probe 650 may be able to detect a malignant tumor volume $V_T$ to be biopsied.

Such substantially real-time optical information may be useful during insertion of the biopsy device 600, for example by providing a linear scan of the tissue as the device 600 is pushed into the tissue. Such optical information may be provided (e.g., displayed on a screen coupled to the processor 510) to the operator (e.g., the surgeon), indicating the likelihood of tissues of interest (e.g., malignant tissue or blood vessel) in the detection volume $V_D$. In addition, the device 600 may be rotated at any point during the insertion to obtain optical information for diseased tissue or blood vessels about the tip 603, akin to a naval periscope.

Once the a suitable biopsy location has been located using the optical spectroscopy probe 650, the optical spectroscopy probe 650 may be positioned away from the biopsy window 630, for example by rotating the inner cannula 610, as shown in FIG. 5C, by pulling back the optical spectroscopy probe 650, or by removing the optical spectroscopy probe 650 from the lumen of the device 600. In some examples, such as where the optical spectroscopy probe 650 has a sufficiently low cross-sectional profile, it may not be necessary to position the optical spectroscopy probe 650 away from the biopsy window 630. A biopsy may be then obtained using appropriate mechanical biopsy techniques. For example, suction may applied (e.g., through the lumen of the inner cannula 610), and the inner cannula 610 may be rotated to excise a biopsy specimen using the cutting edge(s) 625 of the cutting window 620.

Figure 6:
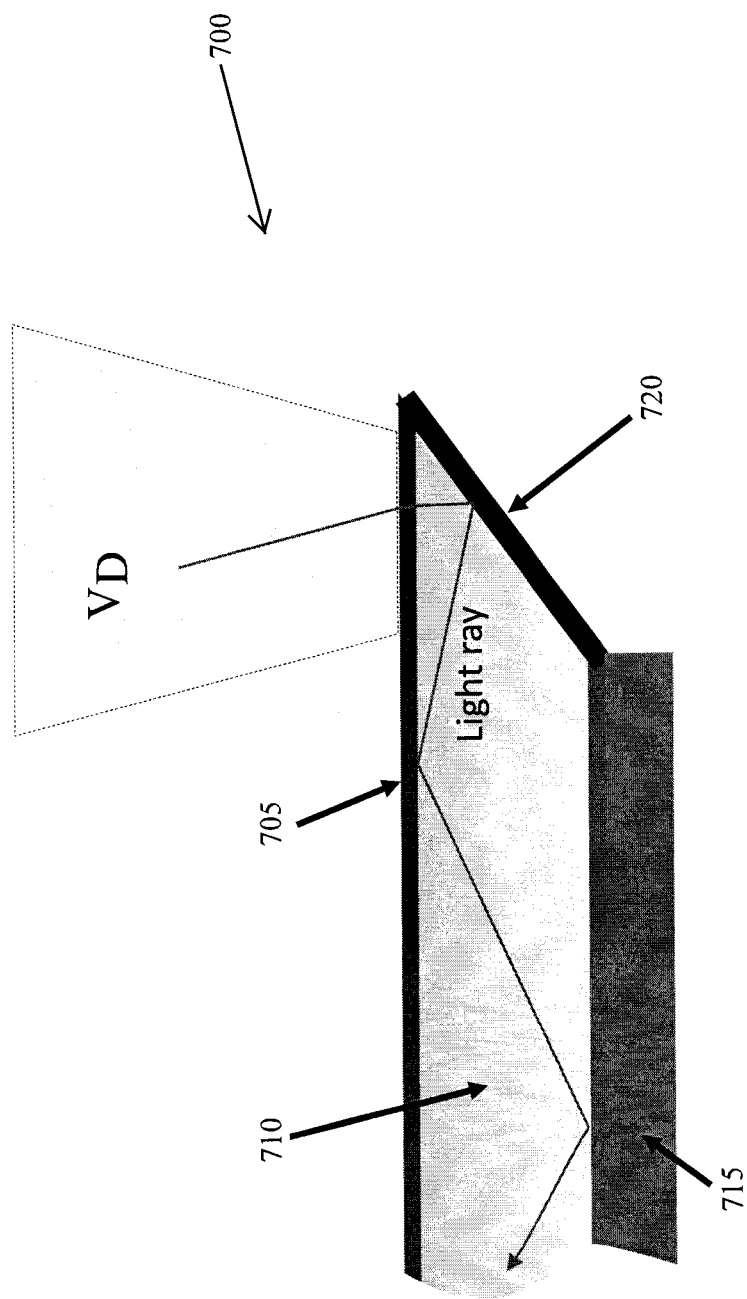
FIG. 6 shows a longitudinal cross-sectional view of an example optical spectroscopy probe having an angled reflective surface.

Designing an optical spectroscopy probe 650 with a configuration suitable for optical spectroscopy guidance from within a biopsy device 600 (e.g., capable of emitting and receiving optical signals at a non-zero angle from its longitudinal axis, for example a transverse detection geometry (e.g., at a 90° detection angle)) may not be simple. The design and fabrication of such a probe 650, for example to achieve the required accuracy, reproducibility and/or manufacturability, may be challenging due to, for example, the need for the probe 650 to fit within a relatively small and restricted space within the biopsy device 600, among other challenges. FIG. 6 shows a close-up view of an example detector 660 configuration achieving this. In this example, the detector 660 may include an optical fiber 700 including a fiber optic glass cladding 705 and a fiber optic core 710. The optical fiber 700 may be supported by a substrate 715, such as a wafer (e.g., a silicon wafer guide). The optical fiber 700 may include an angled (or beveled) fiber end 720, which may be coated with a reflective material. Light rays from a detection volume $V_D$ on the side of the optical fiber may be thus detected in an angled (e.g., 90°) configuration. For example, light rays may pass through the glass cladding 705, reflect off the coating on the angled fiber end 720 and propagate down the optical fiber 700 to provide an optical signal. Similar arrangements may enable the sources 655, 665 to emit side-facing light rays out into the detection volume $V_D$. The light ray geometry may be similar whether light is entering or leaving the fiber optic angled tip.

Creating such a non-zero detection geometry (e.g., creating an angled end 720) and aligning multiple side-firing optical fibers 700 within the limited space of a conventionally-sized biopsy device (e.g., having a diameter of about 2 mm or less) presents challenges. These challenges may include challenges in placement of optical fibers 700, alignment of optical fibers 700, miniaturization and/or reproducibility of fabrication, among others.

The optical fiber 700 for each of the sources 655, 665 and the detector(s) 660, which fiber 700 is typically very thin (for example on the order of about 250 microns in diameter) may need to be positioned in an appropriate fiber chuck in such a way that the fiber end 720 can be configured (e.g., ground down) to the desired angle and polished. Then, a reflective surface may need to be created at the angled end 720 (e.g., by an appropriate silvering process to produce a mirror finish) while avoiding covering (e.g., by the silvering material) the cladding of the fiber end 720.

Figure 11:
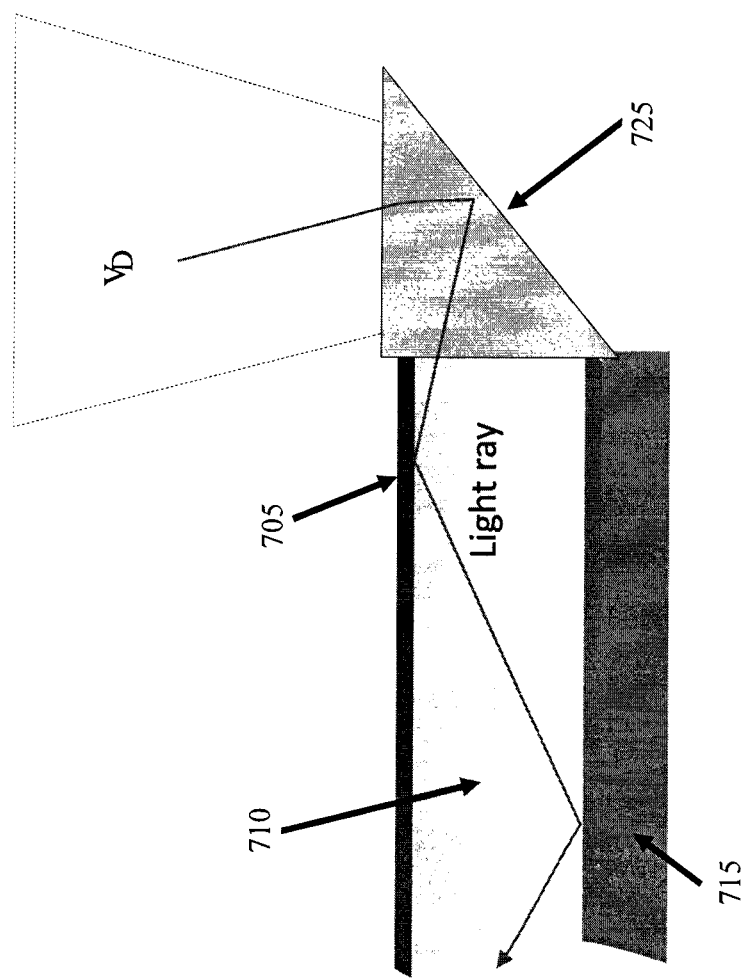
FIG. 11 shows a longitudinal cross-sectional view of an example optical spectroscopy probe having a prism for redirecting light.

Another example embodiment of a suitable side-firing optical fiber 700 is shown in FIG. 11. In this example, an embodiment of the detector 660 is shown. The optical fiber 700 may include a fiber optic glass cladding 705 and a fiber optic core 710. The optical fiber 700, as in FIG. 6, may be held by a substrate 715 that may facilitate alignment and/or provide support for the fiber 700. Instead of a reflective surface at the fiber 720, in this example a reflective microprism 725 (or other light-redirecting element) may be positioned (e.g., optically coupled and/or glued) at the fiber end 720 to redirect incoming light rays (or outgoing light rays, in the case of the sources 655, 665) through the side-facing biopsy window 630. A challenge in this embodiment may be in reproducibly affixing a suitable prism 725 (or other light-redirecting element) at the fiber end 720 while retaining a sufficiently high optical coupling efficiency between the fiber 700 and the prism 720 (e.g., avoiding the situation where the glue between the prism 725 and the fiber end 720 obscures a large portion of the optical signal). As the fiber 700 and its optic components may be extremely miniature (e.g., on the order of a few hundred microns or less), this represents a technical challenge.

Regardless of the configuration of the side-firing optical fiber 700 (e.g., the embodiment shown in FIG. 6, FIG. 11 or other suitable configuration), the multiple side-firing optical fibers 700 for the sources 655, 665 and the detector(s) 660 may then have to be arranged at predefined fixed distances from each other (e.g., in a linear array). In addition to arranging the fibers 700 accordingly, it may be necessary to angularly position each fiber 700 appropriately in order to direct each fiber 700 to emit or receive optical signals through the side-facing biopsy window 630.

The challenges and configurations described above, in order to achieve an optical spectroscopy probe 650 that is capable of emitting and receiving optical signals through a biopsy window 630 of a biopsy device 600, may not be readily achievable or encountered by conventional optical probes (e.g., optical probes that are not integratable into a biopsy device).

Figure 7A:
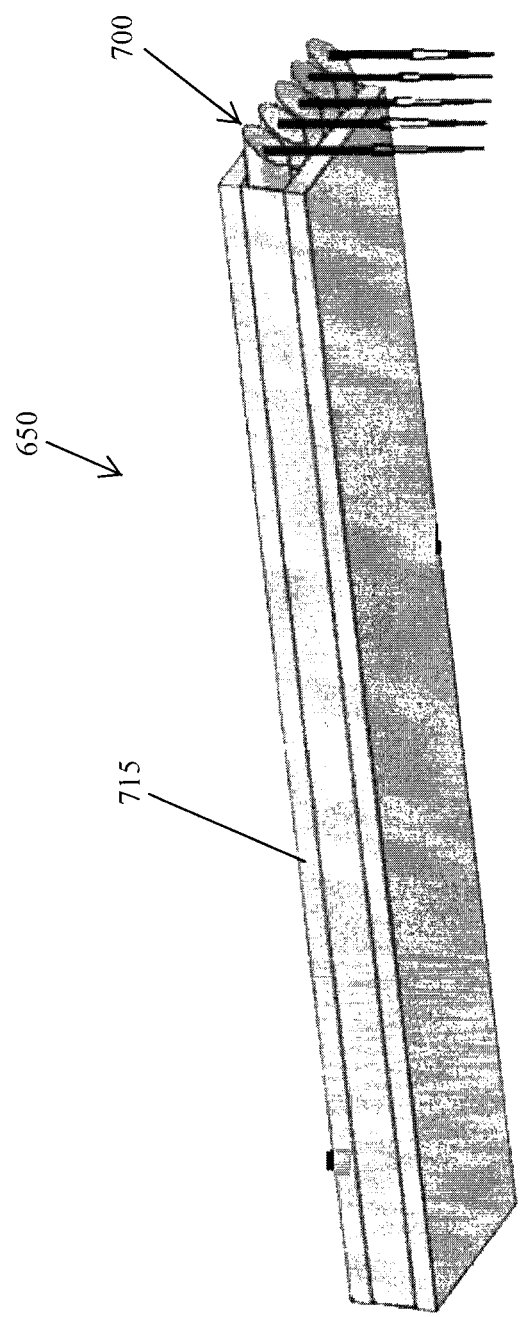
FIG. 7A shows an isometric view of the example optical spectroscopy probe of FIG. 6.
Figure 7B:
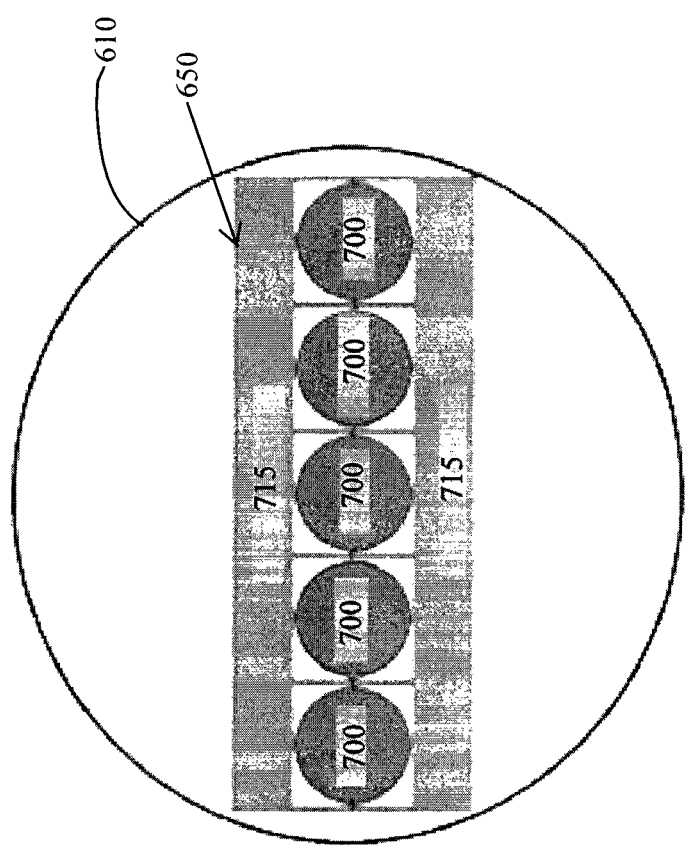
FIG. 7B shows a transverse cross-sectional view of the example optical spectroscopy probe of FIG. 6.

FIGS. 7A, 7B and 8A-8C show an example of how optical fibers 700 may be arranged in the optical spectroscopy probe 650. In the example shown, there may be five optical fibers 700, to serve as one fluorescent excitation source 655, one detector 660 and three broadband light sources 665. The optical fibers 700 may be supported by a substrate 715, such as a silicon wafer holder, to form the optical spectroscopy probe 650. This assembly may be sized and shaped such that the optical spectroscopy probe 650 may be provided in the inner cannula 610 of the biopsy device 600. The fibers 700 may be packaged between two silicon wafers and fixed with respect to each other in order to maintain the known fixed distance from fiber to fiber. FIG. 7A shows an isometric view of the example probe 650 and FIG. 7B shows a cross-sectional view. The role of each fiber 700 may be changeable. Any one or more of the fibers 700 may be independently used as the detector 660 while one or more of the remaining fibers 700 may be used as a source 655, 665 at predetermined wavelength(s) of emission. As shown in FIG. 7A, the fibers 700 may all be aligned and oriented to have substantially the same side-facing orientation (as indicated by arrows).

FIGS. 8A-8C demonstrate the movement of an example inner cannula 610, including an example optical spectroscopy probe 650, relative to the outer cannula 605. As the inner cannula 610 advances within the outer cannula 605 tissue optical properties may be continuously measured using the probe 650. Since the probe 650 in this example has optical fibers 700 fixed on a substrate 715 within the inner cannula 610, moving the inner cannula 610 may be sufficient to allow for collection of optical signals from the probe target along the entire biopsy window 630 of the biopsy device 600.

Figures 10A, 10B:
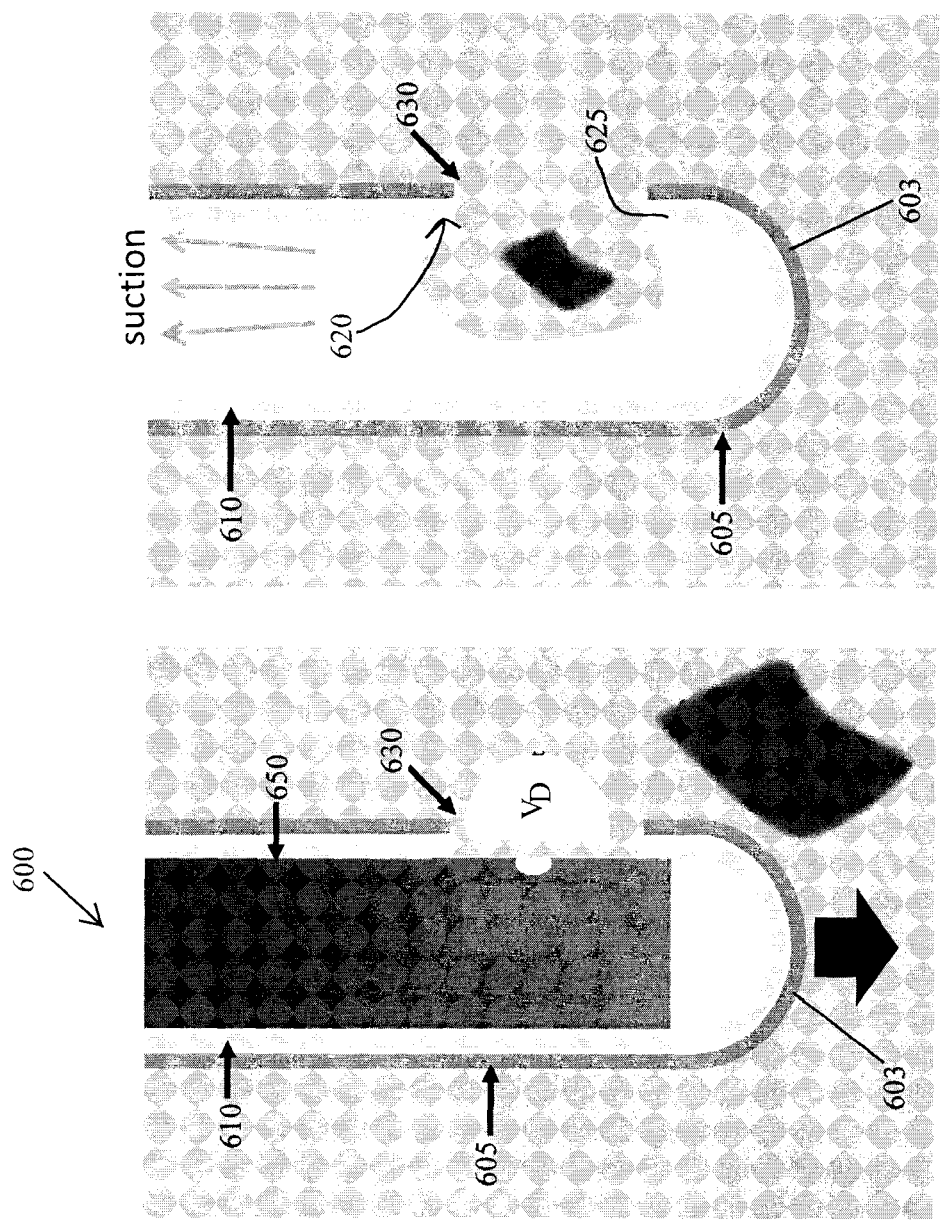
FIGS. 10A and 10B illustrate an example biopsy procedure including use of an example optical spectroscopy probe that is removable from an example biopsy device.

In some examples, as shown in FIGS. 10A and 10B, the optical spectroscopy probe 650 may be removable from the lumen of the biopsy device 600. For example, the fibers 700 of the optical spectroscopy probe 650 may be sufficiently supported by the substrate 715 such that the optical spectroscopy probe 650 may be removably positionable in the lumen of the inner cannula 610. In such a configuration, the optical spectroscopy probe 650 may be provided as an independent component, that may be introduced into any biopsy device (e.g., the needle 100 of FIGS. 1A and 1B), including any conventional biopsy needle (which need not be limited to neural biopsy needles), for providing integrated optical spectroscopy guidance for any suitable biopsy procedure.

In the example shown, the optical spectroscopy probe 650 may be introduced into the lumen of the biopsy device 600 (e.g., the lumen of the inner cannula 610) in order to obtain information about the tissue in the detection volume. The biopsy device 600 may be maneuvered in the tissue (e.g., indicated by the arrow at the distal end 603) while the optical spectroscopy probe 650 is positioned inside, in order to interrogate different areas of the tissue. Once the biopsy target (e.g., a tumor volume $V_T$) is located, the optical spectroscopy probe 650 may be removed and a mechanical biopsy may be obtained as described above (FIG. 10B).

In some examples, the disclosed device 600 may provide an additional safety feature due to its ability to quantify hemoglobin concentration at the point of optical measurement. For example, If a large blood vessel is situated within the detection volume $V_D$ of the probe 650, the calculated hemoglobin concentration, [Hb], will be typically much higher than if the probe 650 were measuring tissue with lower blood vessel density. Thus, the [Hb] signal may be used to provide feedback to warn the surgeon against rupturing large blood vessels during biopsy excision, which may help in reducing the risk of brain hemorrhage, which is one of the major risks of stereotactic brain biopsy.

Figure 9:
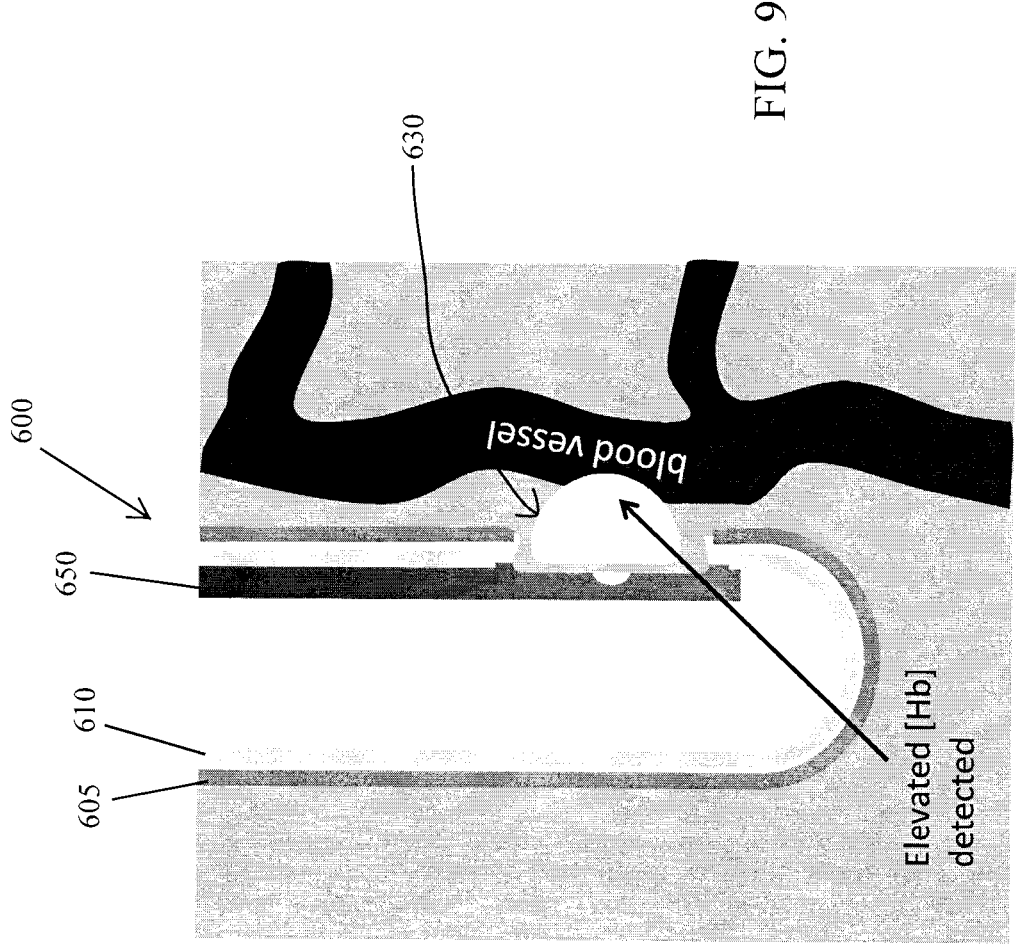
FIG. 9 illustrates the use of an example optical spectroscopy probe in an example biopsy device for detecting a blood vessel.

For example, consider the risk of unintentionally causing hemorrhage and an emergency situation, as shown in FIGS. 2A and 2B. As illustrated in FIG. 9, by using an example of the disclosed biopsy device 600 including an optical spectroscopy probe 650, optical measurements of the tissue prior to biopsy may be obtained, and elevated hemoglobin signals calculated from the optical measurements (e.g., as determined based on calculated optical spectra indicative of hemoglobin) may be found to be indicative of a nearby blood vessel (e.g., the calculated hemoglobin concentration may be higher than a certain predefined threshold) and feedback may be provided to warn the surgeon against excision.

For example, the optical spectroscopy probe 650 may be used to detect a reflectance spectrum from the tissue in the vicinity of the biopsy window 630 (that is, in the detection volume $V_D$). This reflectance spectrum may be communicated to a processor, which may implement an algorithm to analyze the reflectance spectrum based on the known absorption spectrum of hemoglobin (e.g., it may be expected that hemoglobin would have certain known absorption characteristics in the range of about 400 nm to about 800 nm) as well as how the absorption spectrum of hemoglobin would be distorted by absorption and/or scattering of light by other tissues in the detection volume $V_D$. The processor may determine whether the hemoglobin concentration is high enough to indicate the presence of a large blood vessel (e.g., having a diameter of about 0.5 mm or greater) is in the vicinity of the biopsy window 630 (e.g., within about 2 mm or less, which may be within the detection volume $V_D$) and at risk of being damaged if a biopsy were attempted at that location.

The present disclosure may provide a method for characterizing a tissue intended for biopsy. The method may be carried out by an example of the disclosed optical spectroscopy probe 650 and or an example of the disclosed device 600.

The optical spectroscopy probe 650 may be positioned in a lumen of the biopsy device 600, while the biopsy window 630 is positioned in a vicinity of a target tissue intended for biopsy. The optical spectroscopy probe 650 may be controlled (e.g., using the control system 505 and/or the processor 510) to emit and receive optical signals through the biopsy window 630, in order to obtaining an optical spectrum of the target tissue or of a fluorophore coupled to and/or concentrated within the tissue. The obtained optical spectrum may be used (e.g., by the control system 505 and/or the processor 510) to calculate an optical property of the tissue or of the fluorophore, in order to characterize the target tissue as a biopsy target (e.g., a tumor tissue, such as a tumor tissue of high pathological grade) or a tissue to avoid (e.g., a non-tumor tissue or a blood vessel).

If the target tissue is characterized as a tissue to avoid, a notification may be provided (e.g., via one or more output devices coupled to the processor 510) that biopsy should be avoided.

If the target tissue is characterized as a biopsy target, then biopsy of the tissue may be carried out, for example as described above.

In various example aspects and embodiments, the present disclosure may provide a tissue biopsy device, system and method that may integrate optical interrogation of tissue and mechanical sampling of tissue. The device may include a removably or permanently integrated optical spectroscopy probe for obtaining measurements of the fluorescence and optical absorption and scattering properties of a target (e.g., tissues) at multiple wavelengths, for example within a relatively small and/or local detection region lying at depth in the tissue. The probe may be positionable in or included with a mechanical biopsy device so that optical measurements and tissue collection may be done at the same or nearly the same location in the tissue.

The optical measurements may allow the status and/or characteristics of the target (e.g., tissue) to be assessed quantitatively, including presence and degree (e.g., grade) of tumor malignancy, the presence of one or more large blood vessels, the concentration of hemoglobin and oxyhemoglobin, and/or the light scattering characteristics of the tissue, for example. This information on the tissue status and/or characteristics may be measured at multiple locations within the tissue as the probe and/or the biopsy device is advanced into the tissue.

The optical spectroscopy probe may be positionable (e.g., rotated and/or translated) relative to the biopsy window. This may enable the tissue characteristics to be measured at multiple points along and/or across the biopsy window, and the tissue status may be mapped across and/or along this window. This assessment may assist in selection of a preferred site for tissue biopsy (e.g. at the location of the highest-grade of malignancy) and/or may help to reduce or minimize the risk of damaging tissues, such as large blood vessels (e.g., having a diameter of about 0.5 mm or larger) that may lead to hemorrhage. For example, this may allow large blood vessels lying within the detection region to be avoided when the biopsy sample is taken, or the region of maximum malignant grade to be biopsied.

The optical spectroscopy probe may be positioned and may be translated and/or rotated within the biopsy device such as not to interfere with the mechanical sampling (i.e., biopsy) of the tissue.

In some examples, the biopsy device may incorporate a means to locate and read out the position and/or orientation of the optical spectroscopy probe, for example by a graduated scale and/or indicator on the optical spectroscopy probe indicating the location and/or orientation of the probing region of the optical spectroscopy probe with reference to the position and/or orientation of the biopsy window of the biopsy device.

The disclosed devices and methods may provide an ability to characterize the local tissue optically nearly simultaneously with biopsy, for example for the purpose of reducing the duration of the procedure, reducing the number of biopsies required, increasing the likelihood of obtaining biopsy tissue of high tumor grade, and/or increasing the safety of the procedure.

The optical measurement may be based on the use of two or more optical sources displaced at selected and known separations (e.g., either across or along the length of the optical spectroscopy probe) to deliver light locally to the tissue, collect the light from the tissue, and transport the light to one or more photodetector instruments that may include spectral discrimination of the detected light.

The fluorescence measured by the optical spectroscopy probe may be from the natural (e.g., endogenous, auto) fluorescence of the tissue and/or from an administered agent (e.g., a fluorescent marker coupled to and/or concentrated within the tissue).

The concentration of the fluorescent molecules in the tissue may be calculated using the spectral and spatial characteristics of the detected signals, for example processed through one or more signal processing (e.g., optimization) algorithms. For example, the fluorescence emission spectrum may be used to determine the concentration of a fluorophore in the tissue. In the case where the fluorophore is ALA-PpIX, the concentration of PpIX may be used to determine the tumor grade of the tissue.

The algorithms used may be based on one or more biophysical models of the interaction of light with tissue components and fluorescent molecules, for example as described in PCT Publication No. 2011/088571. In the present disclosure, such algorithms may be applied for optical spectroscopy guidance in a biopsy procedure.

The optical fiber light delivery and collection may be in a direction having a non-zero angle to the longitudinal axis of the optical spectroscopy probe, the angle degree may be dependent on the application and/or dependent on the location of the biopsy window.

The present disclosure may provide methods, devices and systems suitable for providing guidance for tumor biopsy, including brain tumor biopsy, using optical spectroscopy.

The present disclosure may enable acquisition of fluorescence information (e.g., substantially real-time, in-situ fluorescence emission information, in the vicinity of the biopsy window of a biopsy device), which information may be used to provide feedback to the operator (e.g., surgeon) about the tissue in the vicinity of the biopsy window. For example, in a tumor biopsy procedure, the present disclosure may enable acquisition of fluorescence information (e.g., from a fluorophore coupled and/or concentrated within to the tissue and/or from the tissue itself where the tissue is capable of fluorescence) that may be used to provide feedback to the surgeon whether the biopsy window is located at a site of high tumor grade, so that obtaining a biopsy of tissue at that location would result in obtaining a biopsy sample having more diagnostically relevant information. This may help to reduce the number of biopsy passes required to obtain an adequate biopsy sample.

A fluorophore, such as ALA-induced PpIX, may be used to label tumor tissues. By obtaining fluorescence emission from the fluorophore coupled to and/or concentrated within the tissue, the concentration of the fluorophore in the vicinity of the biopsy window may be determined, and this concentration may in turn be used as a predictor of the presence and/or grade of tumor tissue in the vicinity of the biopsy window. Other fluorophores may also be used, for example other fluorophores suitable for labeling tumor or other tissues.

The present disclosure may also enable determination of whether the biopsy window is in the vicinity of (e.g., within about 2 mm of) tissue that should be avoided (e.g., a significant blood vessel). For example, in the disclosed methods, devices and systems, acquired reflectance spectrum information may be used to determine (e.g., based on the shape of the reflectance spectrum) an optical property of the target tissue, such as the hemoglobin absorption of the tissue, which may in turn be used to determine whether the target tissue should be avoided. For example, if calculations using the detected reflectance spectrum indicate that the target tissue has a high hemoglobin concentration, this may result in a determination that the target tissue is a tissue that should not be biopsied (e.g., the target tissue is likely to be a blood vessel). A notification (e.g., a warning display or audio tone) may be provided to the operator (e.g., surgeon), so that the operator may avoid taking a tissue sample at that location and thus reduce the risk of a hemorrhage.

The sites and organs in which the disclosed methods, devices and systems may be applied include, for example, the brain, breast, prostate, lung, head and neck, and other solid organs that may be accessible by passing the optical spectroscopy probe or the biopsy device through the overlying tissue.

Other sites and organs may be accessed endoscopically, for example with the optical spectroscopy probe placed directly into the lumen or through a channel of an endoscopic system, and placed on the luminal tissue surface or passed into or through the lumen to reach the tissue of interest. This may be suitable for biopsy procedures performed during endoscopic examination, for example.

The positioning of the optical spectroscopy probe may be directed by various suitable imaging modalities including X-rays, CT, MRI or ultrasound, for example. Such imaging may provide imaging coordinates in a plane or in three dimensions. Three dimensional imaging may be useful for improvement of stereotactic biopsy procedures as used, for example, in neurosurgery.

Example methods suitable for fabricating the optical elements of the optical spectroscopy probe may include the use of lithographically generated elements to allow accurate alignment and/or positioning of the optical fibers in the optical spectroscopy probe.

The embodiments of the present disclosure described above are intended to be examples only. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. P. A. Valdes, F. LeBlond, A. Kim, B. T. Harris, B. C. Wilson, X. Fan, T. D. Tosteson, A. Hartov, S. Ji, K. D. Paulsen, D. W. Roberts. "Quantitative fluorescence in intracranial tumor: implications for ALA-induced PpIX as an intraoperative biomarker," J. Neurosurg. 115(1): 11-7 (2011).
2. A. Kim, B. C. Wilson. "Device, system and method for quantifying fluorescence and optical properties," International Publication Number WO 2011/088571, priority date Jan. 25, 2010.
3. A. Kim, M. Khurana, Y. Moriyama, B. C. Wilson. "Quantification of in vivo fluorescence decoupled from the effects of tissue optical properties using fiberoptic spectroscopy measurements," J Biomed Opt 15, 057006 (2010).
4. A. Kim, M. Roy, F. Dadani, B. C. Wilson. "A fiberoptic reflectance probe with multiple source-collector separations to increase the dynamic range of derived tissue optical absorption and scattering coefficients," Opt Express 18, 5580-5594 (2010).

The invention claimed is:

1. An optical spectroscopy apparatus for providing optical spectroscopy guidance of a mechanical biopsy procedure, the optical spectroscopy apparatus being positionable in a lumen of an outer cannula of a mechanical biopsy device, the optical spectroscopy apparatus comprising:
   an inner cannula positionable in the lumen of the outer cannula, the inner cannula having a cutting window with one or more cutting edges, the inner cannula being positionable to align the cutting window with a biopsy window of the outer cannula; and
   an optical spectroscopy probe integrated with the inner cannula, the optical spectroscopy probe comprising:
      at least one optical detector at a probing region of the optical spectroscopy probe for receiving at least one of fluorescence emission wavelengths and reflectance wavelengths through the biopsy window, the receiving being at least partially along an angled axis that is at a non-zero angle to a longitudinal axis of the optical spectroscopy probe;
      at least one fluorescence excitation source at the probing region for emitting fluorescence excitation light through the biopsy window, at least partially along the angled axis; and
      at least two broadband light sources at the probing region for emitting broadband wavelengths of light through the biopsy window, at least partially along the angled axis;
      wherein each of the at least one fluorescence excitation source and each of the at least two broadband light sources are at a respective known distance from each of the at least one optical detector.

2. The apparatus of claim 1 wherein each of the at least one optical detector, the at least one fluorescence excitation source and the at least two broadband light sources comprise an optical fiber, each optical fiber being configured to redirect emitted light from along the longitudinal axis to at least partially along the angled axis or to redirect received light from along the angled axis to at least partially along the longitudinal axis.

3. The apparatus of claim 2 wherein each optical fiber comprises an optical element for redirecting emitted light or received light.

4. The apparatus of claim 3 wherein the optical element comprises at least one of: a reflective surface, and a prism.

5. The apparatus of claim 1 further comprising a substrate for supporting the at least one fluorescence excitation source and the at least two broadband light sources at the respective known distances from each of the at least one detector.

6. The apparatus of claim 1 wherein at least one of the broadband light sources is at a distance from the at least one detector that is substantially equal to a distance between the at least one fluorescence excitation source and the at least one detector.

7. The apparatus of claim 1 wherein there is one detector, one fluorescence excitation source at a distance of about 260 µm from the detector, and two broadband light sources each at a respective distance of about 260 µm and 520 µm from the detector.

8. The apparatus of claim 1 wherein the fluorescence excitation source is configured to emit fluorescence excitation light in the range of about 350 nm to about 750 nm.

9. The apparatus of claim 1 wherein the fluorescence excitation source is configured to emit fluorescence excitation light in the range of about 380 nm to about 420 nm.

10. The apparatus of claim 1 wherein there is a plurality of fluorescence excitation sources, each of the plurality of fluorescence excitation sources emitting a different range of fluorescence excitation wavelengths.

11. A tissue biopsy device comprising:
an outer cannula defining a biopsy window for obtaining a mechanical biopsy of a probe target;
an inner cannula positionable in a lumen of the outer cannula, the inner cannula having a cutting window with one or more cutting edges, the inner cannula being positionable to align the cutting window with the biopsy window of the outer cannula; and
an optical spectroscopy probe integrated with the inner cannula, the optical spectroscopy probe including a probing region configured to emit and receive optical signals through the biopsy window for obtaining an optical spectrum of the probe target.

12. The biopsy device of claim 11 wherein the optical spectroscopy probe comprises, at the probing region:
at least one optical detector for receiving fluorescence emission or reflectance wavelengths from the probe target;
at least one fluorescence excitation source for emitting fluorescence excitation light to the probe target; and
at least two broadband light sources for emitting broadband wavelengths of light to the probe target;
wherein each of the at least one fluorescence excitation source and each of the at least two broadband light sources are at a known distance from each of the at least one optical detector.

13. The biopsy device of claim 11 wherein
the optical spectroscopy probe is in a lumen of the inner cannula.

14. The biopsy device of claim 11 wherein the optical spectroscopy probe is positionable away from the biopsy window to enable acquisition of a tissue sample through the biopsy window.

15. The biopsy device of claim 11 wherein the optical spectroscopy probe is rotatable within the lumen of the outer cannula.

* * * * *